US012752086B2

(12) United States Patent
Desai et al.

(10) Patent No.: US 12,752,086 B2
(45) Date of Patent: Oct. 6, 2026

(54) SYSTEMS AND METHODS FOR THE CONTROL OF MULTIPLE DEGREES-OF-FREEDOM BENDING AND THE BENDING LENGTH OF A COAXIALLY ALIGNED ROBOTICALLY STEERABLE GUIDEWIRE

(71) Applicant: Georgia Tech Research Corporation, Atlanta, GA (US)

(72) Inventors: Jaydev P. Desai, Atlanta, GA (US); Yash Chetan Chitalia, Atlanta, GA (US); Seokhwan Jeong, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 881 days.

(21) Appl. No.: 17/919,763

(22) PCT Filed: Apr. 21, 2021

(86) PCT No.: PCT/US2021/028493
§ 371 (c)(1),
(2) Date: Oct. 19, 2022

(87) PCT Pub. No.: WO2021/216782
PCT Pub. Date: Oct. 28, 2021

(65) Prior Publication Data

US 2023/0158279 A1 May 25, 2023

Related U.S. Application Data

(60) Provisional application No. 63/013,425, filed on Apr. 21, 2020.

(51) Int. Cl.
*A61M 25/09* (2006.01)

(52) U.S. Cl.
CPC .............................. *A61M 25/09041* (2013.01)

(58) Field of Classification Search
CPC ........ A61M 25/09041; A61M 25/0133; A61M 25/0138; A61M 25/0144; A61M 25/0147; A61B 34/71; A61B 2034/301
See application file for complete search history.

(56) References Cited

U.S. PATENT DOCUMENTS 10,856,855 B2 12/2020 Gordon
11,723,738 B2 * 8/2023 Riojas .................... A61B 34/72 606/1

(Continued)

FOREIGN PATENT DOCUMENTS

EP 3175813 A1 6/2017
JP 2004-351005 A 12/2004

(Continued)

OTHER PUBLICATIONS

Supplemental European Search Report from Application No. 21793176.5 dated May 6, 2024.

(Continued)

*Primary Examiner* — Devin B Henson
(74) *Attorney, Agent, or Firm* — TROUTMAN PEPPER LOCKE LLP; Ryan A. Schneider; Stephanie J. Remy

(57) ABSTRACT

The current disclosure generally relates to systems and methods of guidewire control, and in particular to systems and methods for the control of multiple degrees-of-freedom bending and the bending length of a coaxially aligned robotically steerable guidewire. The current disclosure is manually actuated, and in others, is automatically/robotically actuated.

29 Claims, 17 Drawing Sheets

(56) References Cited

U.S. PATENT DOCUMENTS

| | | | |
|---|---|---|---|
| 11,850,384 | B2 | 12/2023 | Desai et al. |
| 2005/0149159 | A1 | 7/2005 | Andreas et al. |
| 2009/0082722 | A1 | 3/2009 | Munger et al. |
| 2009/0195153 | A1 | 8/2009 | Lee et al. |
| 2011/0160608 | A1 | 6/2011 | Hargrove |
| 2013/0116705 | A1 | 5/2013 | Salahieh et al. |
| 2014/0343457 | A1 | 11/2014 | Shekalim et al. |
| 2018/0070935 | A1 | 3/2018 | Fenech |
| 2019/0083749 | A1 * | 3/2019 | Swaney ............. A61B 17/3417 |
| 2019/0298460 | A1 * | 10/2019 | Al-Jadda .............. A61B 1/0057 |

FOREIGN PATENT DOCUMENTS

| | | | |
|---|---|---|---|
| JP | 2014-516657 | A | 7/2014 |
| JP | 2017-504377 | A | 2/2017 |
| JP | 2020-509848 | A | 4/2020 |
| WO | 2014188403 | A1 | 11/2014 |
| WO | 2018119334 | A | 6/2018 |
| WO | 2018165572 | A1 | 9/2018 |

OTHER PUBLICATIONS

International Search Report and Written Opinion from PCT Application No. PCT/US2021/028493 dated Aug. 6, 2021.

English translation of Office Action issued in Chinese Patent Application No. 202180040388.6, mailed Jun. 21, 2025 (9 pages).

Office Action issued in Chinese Patent Application No. 202180040388.6, mailed Jun. 21, 2025 (26 pages).

Notice of Reasons for Refusal (with English translation) from Japanese Patent Application No. 2022-563876 dated Jan. 23, 2025.

Office Action from Chinese Application No. 202180040388.6 dated Dec. 12, 2024.

Notice of Reasons for Refusal (with English translation) from Japanese Patent Application No. 2022-563876 dated Jul. 15, 2025. (6 Pages).

Examination Report No. 1 from Australian Patent Application No. 2021259459 dated Feb. 24, 2026. (4 Pages).

Notice of Reasons for Refusal (with English translation) in related Korean Patent Application No. 10-2022-7040029 mailed Jan. 20, 2026. (16 Pages).

Examination Report No. 2 in related Australian Patent Application No. 2021259459 mailed Mar. 24, 2026. (5 Pages).

Notice of Reasons for Refusal (with English translation) from Japanese Patent Application No. 2022-563876 dated Sep. 2, 2025. (6 Pages).

* cited by examiner

OUTER TUBULAR ELEMENT 228
INTERMEDIATE TUBULAR ELEMENT 226
INNER TUBULAR ELEMENT 224
TENDON 222
BENDING SEGMENT
NON-BENDING SEGMENT
COAXIALLY ALIGNED STEERABLE GUIDEWIRE
0.400 mm (ID: 0.34 mm)
0.311 mm (ID: 0.24 mm)
0.203 mm (ID: 0.101 mm)
0.078 mm
0.400 mm

MINIATURE FORCE SENSOR
EM TRACKER
LINEAR MOTORS
LINEAR MOTORS
LINEAR MOTORS
LINEAR MOTORS
LEADSCREW
SHAFT/SLIDER
BASE LINEAR MOTOR
LINEAR GUIDE

SYSTEMS AND METHODS FOR THE CONTROL OF MULTIPLE DEGREES-OF-FREEDOM BENDING AND THE BENDING LENGTH OF A COAXIALLY ALIGNED ROBOTICALLY STEERABLE GUIDEWIRE

CROSS-REFERENCE TO RELATED APPLICATIONS

This application is a §371 National Stage of International Patent Application No. PCT/US2021/028493, with an international filing date of 21 Apr. 2021, which International Patent Application No. PCT/US2021/028493 claims the benefit under 35 USC § 119(e) of U.S. Provisional Patent Application No. 63/013,425 filed 21 Apr. 2020, the entirety of each of which is incorporated herein by reference as if fully set forth below.

STATEMENT REGARDING FEDERALLY SPONSORED RESEARCH OR DEVELOPMENT

This invention was made with government support under HL144714 awarded by the National Institutes of Health. The government has certain rights in the invention.

THE NAMES OF THE PARTIES TO A JOINT RESEARCH AGREEMENT

Not Applicable

SEQUENCE LISTING

Not Applicable

STATEMENT REGARDING PRIOR DISCLOSURES BY THE INVENTOR OR A JOINT INVENTOR

Not Applicable

BACKGROUND OF THE DISCLOSURE

1. Field of the Invention

The current disclosure generally relates to systems and methods of guidewire control, and in particular to systems and methods for the control of multiple degrees-of-freedom bending and the bending length of a coaxially aligned robotically steerable guidewire.

2. Description of Related Art

Cardiovascular diseases (CVDs) such as chronic heart disease, stroke, or high blood pressure are among the top ten leading causes of death in the US, resulting in direct and indirect costs of about $330 billion in 2014. The minimally invasive treatment of most CVDs begins with the clinician inserting a guidewire from a suitable location in the patient's vasculature and navigating it to the blocked (or diseased) blood vessel. In most procedures for treating peripheral arterial disease (PAD), the operating surgeon must use a variety of catheters riding on the guidewire. These catheters may be equipped with either the tools to perform the atherectomy, such as a micro-drill, or a drug delivery unit (in the form of a drug-coated balloon) to help prevent further deposition on that artery.

The guidewire is a passive wire, typically made of Nitinol, with a diameter of 0.3556 mm-0.889 mm (typical wires are in the range of 0.3556 mm-0.4572 mm or commonly referred to as the 0.014" to 0.018" guidewire) and a length of 50 cm-260 cm depending on intervention paths. Once the guidewire is navigated to the blocked vasculature, the clinician can use the wire as a carrier for a variety of catheters that help to clear the blockage.

The physician manually maneuvers the guidewire to the target artery by proximal insertion, retraction, and rotation (being the only degrees-of-freedom (DoFs) available to the clinician to control the distal tip) of the wire base, while observing its movement on a real-time fluoroscopic image. Such dexterous navigation of the guidewire tip under two-dimensional visual feedback is difficult and time consuming and requires significant experience. Further, angulation, vessel tortuosity, or calcification of the blood vessel can make this control challenging and can result in kinking and breakage of the guidewire.

Changing the wire to an alternate guidewire with a different stiffness/curvature is possible but requires multiple sets of guidewires and the repeated replacement could cause vascular trauma. These challenges in the manual navigation result in increased procedure times and radiation exposure for the patient, clinician, and the operating room staff.

Conventional steerable guidewires and micro-catheters have limitations. Due to the size constraints on the wire diameter, a majority of these are manually actuated or automatically/robotically actuated externally using for example, a magnetic source or are tendon driven. The bulky setup required for magnetic actuation may interfere with imaging modalities such as fluoroscopy and magnetic resonance imaging (MRI). Tendon driven designs have fixed joint lengths and do not perform any sort of "follow-the-leader" motion making it difficult for these wires to navigate into tortuous anatomical paths.

To implement the follow-the-leader motion, conventional tendon-driven continuum robots have an extensible bending section. However, its limited range of extensible length makes it difficult to achieve an ideal follow-the-leader motion and its dimension/complexity makes it unfeasible with guidewire applications.

Conventional mechanisms such as concentric tube assemblies allow the curvature and bending angle of the robot to be varied with increasing joint length, but suffer from complex modeling and instabilities arising from the presence of multiple minimum energy states resulting in the robot 'snapping' from one minimum energy state to another during operation, which can result in inadvertent trauma to the patient.

One innovative way to avoid these problems is via the introduction of notch structures within the individual tubular elements.

However, in all conventional designs, coupling between the joint lengths and bending angle of the systems is retained, i.e. the bending length and the bending angle of these systems cannot be individually controlled.

Thus, technological innovation is needed to provide systems and methods of guidewire control that overcome the limitations of the conventional systems and methods. Thus, one focus of the present invention is to provide a tendon-driven coaxially aligned steerable guidewire robot that can simultaneously and independently control the bending angle and the length of the bending segment, thereby executing 'follow-the-leader' motion at its distal bending segment.

BRIEF SUMMARY OF THE INVENTION

Briefly described, according to exemplary embodiments of the present invention, systems and methods of an innovative coaxially aligned steerable guidewire that is sized for a vascular system and provides variable curvature and independently controlled bending length of the distal end. In some exemplary embodiments, the present invention is manually actuated, and in others, is automatically/robotically actuated.

In an exemplary embodiment of the present invention, a robotic system comprises three coaxially aligned hollow bodies, or tubes, with a single tendon running centrally through the length of the robot. The tendon comprises a superelastic wire. A superelastic material may include any material that can deform reversibly to strains of up to about 10%. For instance, in some embodiments, the various components of the present invention can be composed of Nitinol. However, it is understood that various components of the present invention can be composed of any material, and if used in a bio environment, the material can include biocompatible materials that are not necessarily superelastic, including but not limited to biocompatible metals, biocompatible alloys, biocompatible plastics, or materials comprising biocompatible coatings, and the like. Other biocompatible materials may include, for example and not limited to, titanium, or stainless steel, and the like. In an exemplary embodiment, the outer tubular elements are made from micro-machined Nitinol allowing for tendon-driven bending of the robot at various segments of the robot, thereby enabling variable bending curvatures, while an inner stainless-steel tube controls the bending length of the robot. By varying relative positions of the tubes and the tendon by insertion and retraction in the entire assembly, various joint lengths and curvatures can be achieved, which enables a follow-the-leader motion. A controller controls the distal tip of the robot.

The entire robot assembly can be miniaturized to a total outer diameter in the range suitable for use as a micro-scale steerable robotic guidewire. The guidewire can advance its distal end through complex vasculature of varying curvatures with minimal interaction and support from the vessel walls. The present invention can implement a vascular intervention procedure with a guidewire navigation system, thus avoiding replacements of alternate guidewires, which significantly reduces the operational time and effort. In some embodiments, for example, where the guidewire is used through an artery, the guidewire tip can have a width of from about 0.1 mm to about 0.9 mm. In some embodiments, the width of the guidewire tip can be about 0.3, about 0.33 mm, about 0.35 mm, about 0.4 mm, about 0.45 mm, about 0.50 mm, about 0.55 mm, about 0.60 mm, about 0.65 mm, about 0.7 mm, about 0.75 mm, about 0.78 mm, about 0.8 mm, about 0.85 mm, about 0.88, about 0.89 mm, or about 0.9 mm. In some embodiments the width of the guidewire can be from about 0.31 mm to about 0.34 mm, about 0.36 mm to about 0.39 mm, about 0.41 mm to about 0.44 mm, about 0.46 mm to about 0.49 mm, about 0.51 mm to about 0.54 mm, about 0.56 mm to about 0.59 mm, about 0.61 mm to about 0.64 mm, about 0.66 mm to about 0.69 mm, about 0.71 mm to about 0.74 mm, about 0.76 mm to about 0.79 mm, about 0.81 mm to about 0.84 mm, or about 0.86 mm to about 0.89 mm. In an embodiment, the guidewire tip can have a width of greater than about 1.0 mm. For example, in pediatric neurosurgeries, endoscopic tools with a width of about 2.0 mm can be used.

In another exemplary embodiment of the present invention, a robotically steerable guidewire system comprises a path-providing guide comprising a coaxial arrangement of tubular elements and a tendon connected to one of the tubular elements, wherein the path-providing guide has a proximal portion and a distal portion, the path-providing guide configured to locate a distal end of a guidewire to a destination, and a control unit operably connected to the path-providing guide and configured to one or more, control the relative axial alignment of the tubular elements, control the relative lateral alignment of the tubular elements, control the relative rotational alignment of the tubular elements, and control a stroke of the tendon, wherein the path-providing guide and control unit are cooperatively configured to simultaneously and independently control curvature of the distal portion of the path-providing guide and control an arc length of the distal portion of the path-providing guide.

One inventive feature of the present invention is the adjustment of the stiffness/compliance along the length of the path-providing guide generally becoming less stiff from its proximal end to its distal end, providing the distal end with innovative control over both its curvature and its bending length. This can be done in numerous ways. Various segments of the path-providing guide can have a relatively uniform stiffness along its length, wherein the stiffness is adjustable over the length of the path-providing guide in discrete "steps" via the segments. Stiffness can also be controlled by stiffness features of various types on/in one or more tubular elements. For example, the wall thickness of a tubular element can vary along its length to provide a changing stiffness profile along the length of a segment, and thus along the length of the path-providing guide. The stiffness profile can be changed with a variety of other mechanisms, for example, changes in cross-sectional profile, changes of material make-up of a segment, a first material (mix of materials) having a first stiffness and another portion of the path-providing guide/a segment comprising a second material (mix of materials) having a second stiffness. In another exemplary embodiment, the stiffness features can comprise notches/a set of notches along a portion of the length of a tubular element. The sets of notches can have the same length, or different lengths.

The coaxial arrangement of tubular elements can comprise an inner tubular element with an inner channel, an intermediate tubular element having a stiffness feature comprising a set of notches along at least a portion of the length of the intermediate tubular element, and an outer tubular element having a stiffness feature comprising a set of notches along at least a portion of the length of the outer tubular element, wherein the tubular elements each have suitable cross-sectional dimensions such that a guidewire is rotationally and laterally displaceable within the inner channel of the inner tubular element, the inner tubular element is rotationally and laterally displaceable within the intermediate tubular element, and the intermediate tubular element is rotationally and laterally displaceable within the outer tubular element.

The interplay between the sets of notches is useful to vary the stiffness of the path-providing guide along its length, generally becoming less stiff from its proximal end to its distal end, providing the distal end with innovative control over both its curvature and its bending length. The sets of notches can have the same length, or different lengths. The intermediate tubular element can have a length defined from a proximal end to a distal end, and the set of notches begin at an intermediate location of the intermediate tubular element and extend to the distal end of the intermediate tubular element.

The outer tubular element can have a length defined from a proximal end to a distal end, and the set of notches begin at an intermediate location of the outer tubular element and extend to the distal end of the outer tubular element.

The length of the set of notches of the outer tubular element can be the same as the length of the set of notches of the intermediate tubular element, or they can be different. For example, in an exemplary embodiment, the length of the set of notches of the outer tubular element is greater than the length of the set of notches of the intermediate tubular element.

The set of notches of the outer tubular element can have the same phase, or have a phase difference, from the set of notches of the intermediate tubular element. Having a different phase can facilitate the operational independence of intermediate tubular element from the outer tubular element, for example, enabling the intermediate tubular element to be operationally rotational and laterally displaceable within the outer tubular element.

For example, the sets of notches can be offset from one another by 5°, 10°, 15°, 20°, 35°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, or 180°. In some embodiments, the sets of notches can be offset from one another by from 1 to 5°, from 6 to 10°, from 11 to 15°, from 16 to 20°, from 21 to 25°, from 26 to 30°, from 30 to 45°, from 45 to 60°, from 60 to 75°, from 75 to 90°, from 90 to 100°, from 100 to 120°, from 120 to 135°, from 135 to 150°, from 150 to 160°, from 160 to 175°, or from 175 to 180°. The phase(s) of notches of a single set can also vary.

The individual notches can be any geometric shape. In an exemplary embodiment, the recesses can be rectangular. In other embodiments, the recesses can be, for example, sinusoidal or triangular-shaped. In some embodiments, the plurality of recesses can be different shapes. In other embodiments, the sets of notches can have different shapes between each set (one set having one shape, and another set having a different shape), while the shapes of notches within a single set can be different. For example, within a single set of notches, there could be rectangular notches for a portion, a sinusoidal notches for a portion, and triangular notches for a portion, and/or the pitch of notches in a single set could also vary along the length. Essentially, notch geometry can vary along the length of an element. In an embodiment, the shape of the recesses can be selected from the group consisting of rectangular, sinusoidal, semi-circular, or triangular.

The sets of notches can form unidirectional asymmetric notch joints of the intermediate tubular element and the outer tubular element. Notches that are asymmetric can be described as notches that can cause the neutral bending plane of the device to be offset towards an outer edge of the device as opposed to down a central axis of the device, which is generally seen with symmetric notches. An asymmetric pattern of notches can allow the guidewire tip to be bent with a longer moment arm in one direction in the plane of the notches cut, thus allowing a larger range of motion.

The guidewire tip can be defined by a width and a length. The notches can be defined by a depth. In some embodiments, the depth of the notches can be greater than 50% of the width of the guidewire tip. In some embodiments, the depth of the notches can be about 55%, about 60%, about 65%, about 70%, about 75%, about 80%, about 85%, about 90%, or about 95% the width of the guidewire tip. In some embodiments, the depth of the notches can be from about 51% to about 54%, about 56% to about 59%, about 61% to about 64%, about 66% to about 69%, about 71% to about 74%, about 76% to about 79%, about 81% to about 84%, about 86% to about 89%, or about 91% to about 94% the width of the guidewire tip. In other embodiments, the depth of the notches can be 50% or less of the width of the guidewire tip. For instance, in some embodiments, the depth of the notches can be about 10%, about 15%, about 20%, about 25%, about 30%, about 35%, about 40%, about 45%, or about 50% the width of the guidewire tip. In some embodiments, the depth of the notches can be from about 11% to about 14%, about 16% to about 19%, about 21% to about 24%, about 26% to about 29%, about 31% to about 34%, about 36% to about 39%, about 41% to about 44%, or about 46% to about 49% the width of the guidewire tip. Indeed, in some embodiments, not every notch in the plurality of notches need have the same depth such that the depth can vary between the notches. In an embodiment, the notches can be co-located and do not exceed 50% of the width of the tubular element. In other embodiments, the notches can be co-located and can exceed 50% of the width of the tubular element. In embodiments with co-located notches, the notches can be about 25% of the circumferences of the tubular element body. In an embodiment with co-located notches, the joint can move in both degrees-of-freedom due to the notches being in the same location.

The path-providing guide can further have an intermediate portion, wherein the stiffness of the proximal portion of the path-providing guide is greater than the stiffness of the intermediate portion of the path-providing guide, and wherein the stiffness of the intermediate portion of the path-providing guide is greater than the stiffness of the distal portion of the path-providing guide.

The stiffness of each portion of the path-providing guide can be controllable by the relative axial alignment of the tubular elements, the relative lateral alignment of the tubular elements, the relative rotational alignment of the tubular elements, and the stroke of the tendon, such that the proximal portion of the path-providing guide is a length of the path-providing guide comprising the coaxial arrangement of a first portion of inner tubular element, a first portion of the intermediate tubular element that is without the set of notches, and a first portion of the outer tubular element that is with the set of notches, the intermediate portion of the path-providing guide is a length of the path-providing guide comprising the coaxial arrangement of a second portion of the inner tubular element, a second portion of the intermediate tubular element that is with the set of notches, and a second portion of the outer tubular element that is with the set of notches, wherein the first portion and the second portion of the inner tubular element comprise the full length of the inner tubular element, and the distal portion of the path-providing guide is a length of the path-providing guide comprising the coaxial arrangement of a third portion of the intermediate tubular element that is with the set of notches, and a third portion of the outer tubular element that is with the set of notches.

In some embodiments, the present invention is a portion of an overall guidewire system, only located at the distal portion to provide the beneficial compliance control. That is, the present invention need not incorporate from beginning to end the inventive features but be more like a “quick-connect” to an end portion of another device. The invention can therefore be “retro-fit” onto a previous setup to provide the beneficial capabilities of the present invention to an otherwise conventional system.

In another exemplary embodiment of the present invention, a steerable guidewire system comprises a path-providing guide comprising a proximal portion and a distal portion, the path-providing guide configured to locate a distal end of a guidewire to a destination, and a control unit operably connected to the path-providing guide, wherein the path-providing guide and control unit are cooperatively configured to simultaneously and independently control curvature of the distal portion of the path-providing guide, and control an arc length of the distal portion of the path-providing guide.

The path-providing guide can comprise a coaxial arrangement of tubular elements, and a tendon connected to one of the tubular elements, and the control unit can be configured to one or more control the relative axial alignment of the tubular elements, control the relative lateral alignment of the tubular elements, control the relative rotational alignment of the tubular elements, and control a stroke of the tendon.

The stiffness of the proximal portion of the path-providing guide can be greater than the stiffness of the distal portion of the path-providing guide.

In another exemplary embodiment of the present invention, a robotically steerable guidewire system comprises a path-providing guide comprising at least three tubular elements, an inner tubular element with an inner channel, a first intermediate tubular element having a stiffness feature along at least a portion of the length of the first intermediate tubular element, a second intermediate tubular element having a stiffness feature along at least a portion of the length of the second intermediate tubular element (and potentially other intermediate tubular elements) and an outer tubular element having a stiffness feature along at least a portion of the length of the outer tubular element. As noted, in this embodiment, the path-providing guide can comprise of a number of intermediate tubular elements.

A control module is operably connected to the path-providing guide, wherein the control module is configured to laterally displace the relative position of the inner tubular element to the first intermediate tubular element, rotationally displace the relative position of the first intermediate tubular element to the outer intermediate tubular element, and laterally displace the relative position of the outer tubular element to the first intermediate tubular element, wherein one of more of the displacements of the tubular elements results in at least three zones of stiffness along the length of the path-providing guide, a proximal zone having a greater stiffness than an intermediate zone, and the intermediate zone having a greater stiffness than an distal zone, wherein a guidewire is operationally configurable to traverse the length of path-providing guide and be directed to a destination via the variable flexibility and arc length of the distal zone of the path-providing guide.

In another exemplary embodiment of the present invention, a method of manipulating a tip of a guidewire to a destination along a tortuous path comprises feeding the guidewire through a path-providing guide having a distal portion through which the tip of the guideway is configured to exit, and simultaneously and independently controlling along the tortuous path the curvature of the distal portion of the path-providing guide, and an arc length of the distal portion of the path-providing guide.

The path-providing guide can comprise a coaxial arrangement of tubular elements and a tendon connected to one of the tubular elements, and the simultaneously and independently controlling can comprise one or more of controlling the relative axial alignment of the tubular elements, controlling the relative lateral alignment of the tubular elements, controlling the relative rotational alignment of the tubular elements, and controlling a stroke of the tendon.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

Implementations, features, and aspects of the disclosed technology are described in detail herein and are considered a part of the claimed disclosed technology. Other implementations, features, and aspects can be understood with reference to the following detailed description, accompanying drawings, and claims. Wherever possible, the same reference numbers are used throughout the drawings to refer to the same or like elements of an embodiment. Reference will now be made to the accompanying figures and flow diagrams, which are not necessarily drawn to scale.

(FIG. 9).

FIGS. 15A, 15B, 15C show three samples with varying depths of intermediate and outer tubes demonstrate varying coupling between the bending and non-bending segments.

DETAILED DESCRIPTION OF THE INVENTION

Figure 1:
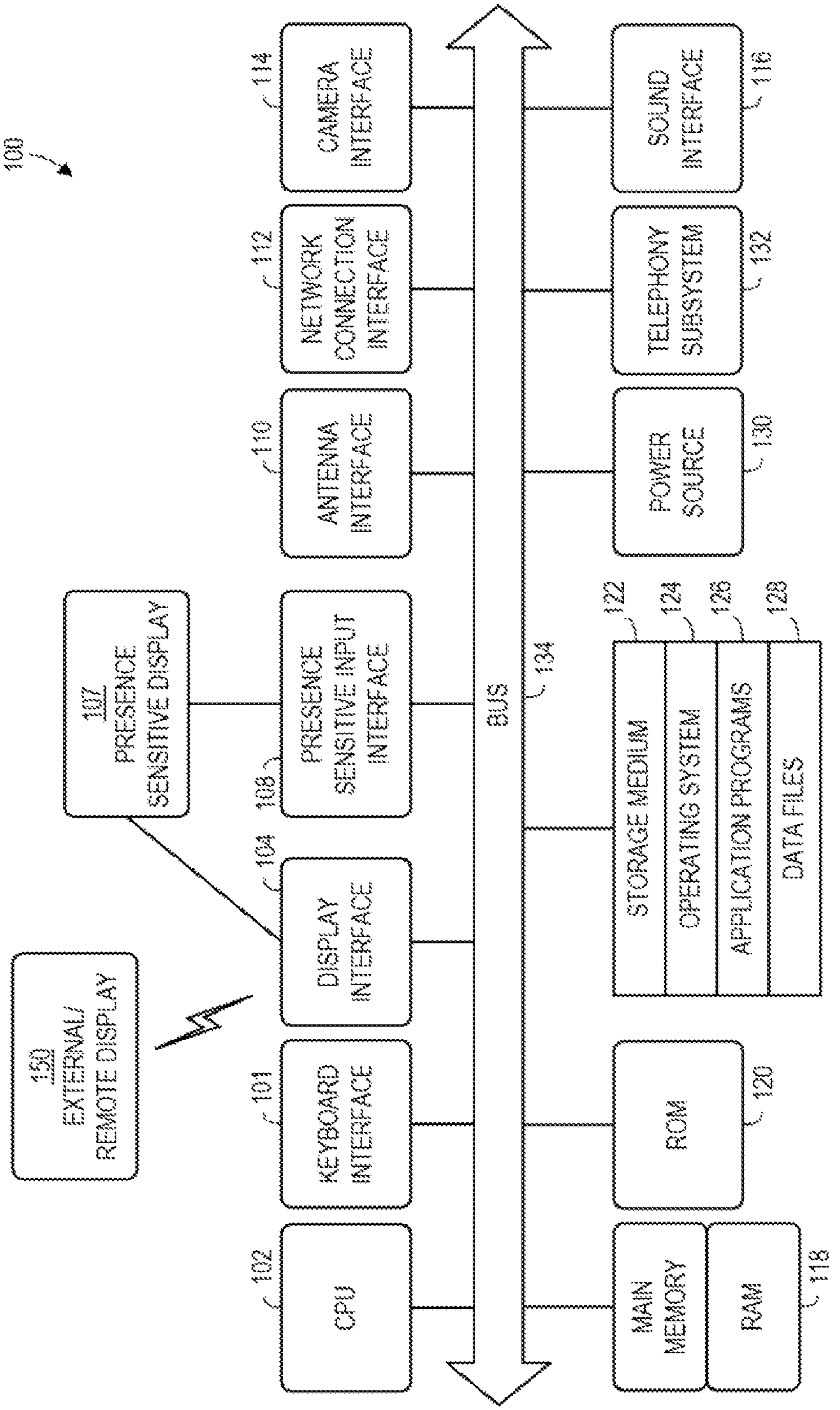
FIG. 1 is a block diagram of an illustrative computer system architecture 100, according to an exemplary embodiment.

Although preferred exemplary embodiments of the disclosure are explained in detail, it is to be understood that other exemplary embodiments are contemplated. Accordingly, it is not intended that the disclosure is limited in its scope to the details of construction and arrangement of components set forth in the following description or illustrated in the drawings. The disclosure is capable of other exemplary embodiments and of being practiced or carried out in various ways. Also, in describing the preferred exemplary embodiments, specific terminology will be resorted to for the sake of clarity.

As used in the specification and the appended claims, the singular forms "a," "an" and "the" include plural referents unless the context clearly dictates otherwise.

Also, in describing the preferred exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another exemplary embodiment includes from the one particular value and/or to the other particular value.

Using "comprising" or "including" or like terms means that at least the named compound, element, particle, or method step is present in the composition or article or method, but does not exclude the presence of other compounds, materials, particles, method steps, even if the other such compounds, material, particles, method steps have the same function as what is named.

Mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Aspects of the disclosed technology may be implementing using at least some of the components illustrated in the computing device architecture 100 of FIG. 1. As shown, the computing device architecture includes a central processing unit (CPU) 102, where computer instructions are processed; a display interface 104 that acts as a communication interface and provides functions for rendering video, graphics, images, and texts on the display. In certain example implementations of the disclosed technology, the display interface 104 may be directly connected to a local display, such as a touch-screen display associated with a mobile computing device. In another example implementation, the display interface 104 may be configured for providing data, images, and other information for an external/remote display that is not necessarily physically connected to the mobile computing device. For example, a desktop monitor may be utilized for mirroring graphics and other information that is presented on a mobile computing device. In certain example implementations, the display interface 104 may wirelessly communicate, for example, via a Wi-Fi channel or other available network connection interface 112 to the external/remote display.

In an example implementation, the network connection interface 112 may be configured as a communication interface and may provide functions for rendering video, graphics, images, text, other information, or any combination thereof on the display. In one example, a communication interface may include a serial port, a parallel port, a general purpose input and output (GPIO) port, a game port, a universal serial bus (USB), a micro-USB port, a high definition multimedia (HDMI) port, a video port, an audio port, a Bluetooth port, a near-field communication (NFC) port, another like communication interface, or any combination thereof. In one example, the display interface 104 may be operatively coupled to a local display, such as a touch-screen display associated with a mobile device. In another example, the display interface 104 may be configured to provide video, graphics, images, text, other information, or any combination thereof for an external/remote display that is not necessarily connected to the mobile computing device. In one example, a desktop monitor may be utilized for mirroring or extending graphical information that may be presented on a mobile device. In another example, the display interface 104 may wirelessly communicate, for example, via the network connection interface 112 such as a Wi-Fi transceiver to the external/remote display.

The computing device architecture 100 may include a keyboard interface 106 that provides a communication interface to a keyboard. In one example implementation, the computing device architecture 100 may include a presence-sensitive display interface 108 for connecting to a presence-sensitive display 107. According to certain example implementations of the disclosed technology, the presence-sensitive display interface 108 may provide a communication interface to various devices such as a pointing device, a touch screen, a depth camera, etc. which may or may not be associated with a display.

The computing device architecture 100 may be configured to use an input device via one or more of input/output interfaces (for example, the keyboard interface 106, the display interface 104, the presence sensitive display interface 108, network connection interface 112, camera interface 114, sound interface 116, etc.,) to allow a user to capture information into the computing device architecture 100. The input device may include a mouse, a trackball, a directional pad, a track pad, a touch-verified track pad, a presence-sensitive track pad, a presence-sensitive display, a scroll wheel, a digital camera, a digital video camera, a web camera, a microphone, a sensor, a smartcard, and the like. Additionally, the input device may be integrated with the computing device architecture 100 or may be a separate device. For example, the input device may be an accelerometer, a magnetometer, a digital camera, a microphone, and an optical sensor.

Example implementations of the computing device architecture 100 may include an antenna interface 110 that provides a communication interface to an antenna; a network connection interface 112 that provides a communication interface to a network. As mentioned above, the display interface 104 may be in communication with the network connection interface 112, for example, to provide information for display on a remote display that is not directly connected or attached to the system. In certain implementations, a camera interface 114 is provided that acts as a communication interface and provides functions for capturing digital images from a camera. In certain implementations, a sound interface 116 is provided as a communication interface for converting sound into electrical signals using a microphone and for converting electrical signals into sound using a speaker. According to example implementations, a random-access memory (RAM) 118 is provided, where computer instructions and data may be stored in a volatile memory device for processing by the CPU 102.

According to an example implementation, the computing device architecture 100 includes a read-only memory (ROM) 120 where invariant low-level system code or data for basic system functions such as basic input and output (I/O), startup, or reception of keystrokes from a keyboard are stored in a non-volatile memory device. According to an example implementation, the computing device architecture 100 includes a storage medium 122 or other suitable type of memory (e.g. such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives), where the files include an operating system 124, application programs 126 (including, for example, a web browser application, a widget or gadget engine, and or other applications, as necessary) and data files 128 are stored. According to an example implementation, the computing device architecture 100 includes a power source 130 that provides an appropriate alternating current (AC) or direct current (DC) to power components.

According to an example implementation, the computing device architecture 100 includes and a telephony subsystem 132 that allows the device 100 to transmit and receive sound over a telephone network. The constituent devices and the CPU 102 communicate with each other over a bus 134.

According to an example implementation, the CPU 102 has appropriate structure to be a computer processor. In one arrangement, the CPU 102 may include more than one processing unit. The RAM 118 interfaces with the computer bus 134 to provide quick RAM storage to the CPU 102 during the execution of software programs such as the operating system application programs, and device drivers. More specifically, the CPU 102 loads computer-executable process steps from the storage medium 122 or other media into a field of the RAM 118 in order to execute software programs. Data may be stored in the RAM 118, where the data may be accessed by the computer CPU 102 during execution. In one example configuration, the device architecture 100 includes at least 98 MB of RAM, and 256 MB of flash memory.

The storage medium 122 itself may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, an external mini-dual in-line memory module (DI MM) synchronous dynamic random-access memory (SDRAM), or an external micro-DI MM SDRAM. Such computer readable storage media allow a computing device to access computer-executable process steps, application programs and the like, stored on removable and non-removable memory media, to off-load data from the device or to upload data onto the device. A computer program product, such as one utilizing a communication system may be tangibly embodied in storage medium 122, which may comprise a machine-readable storage medium.

According to one example implementation, the term computing device, as used herein, may be a CPU, or conceptualized as a CPU (for example, the CPU 102 of FIG. 1). In this example implementation, the CPU may be coupled, connected, and/or in communication with one or more peripheral devices, such as display. In another example implementation, the term computing device, as used herein, may refer to a mobile computing device such as a smartphone, tablet computer, or smart watch. In this example embodiment, the computing device may output content to its local display and/or speaker(s). In another example implementation, the computing device may output content to an external display device (e.g., over Wi-Fi) such as a TV or an external computing system.

Figure 2:
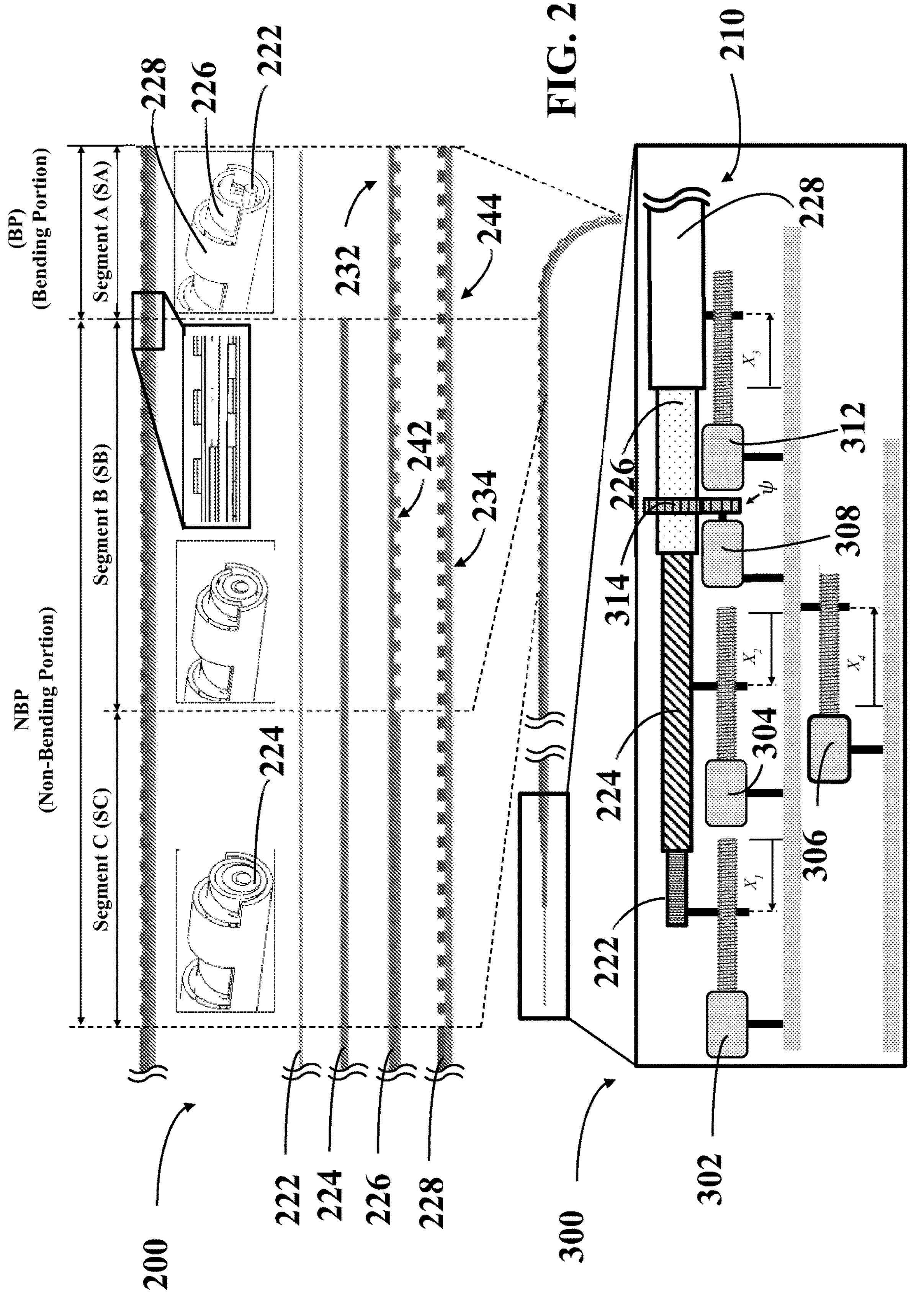
FIG. 2 is a schematic of the present invention according to an exemplary embodiment illustrating the various tubular elements and the actuation module used to control the tendon and coaxial tubular elements.
Figure 3:
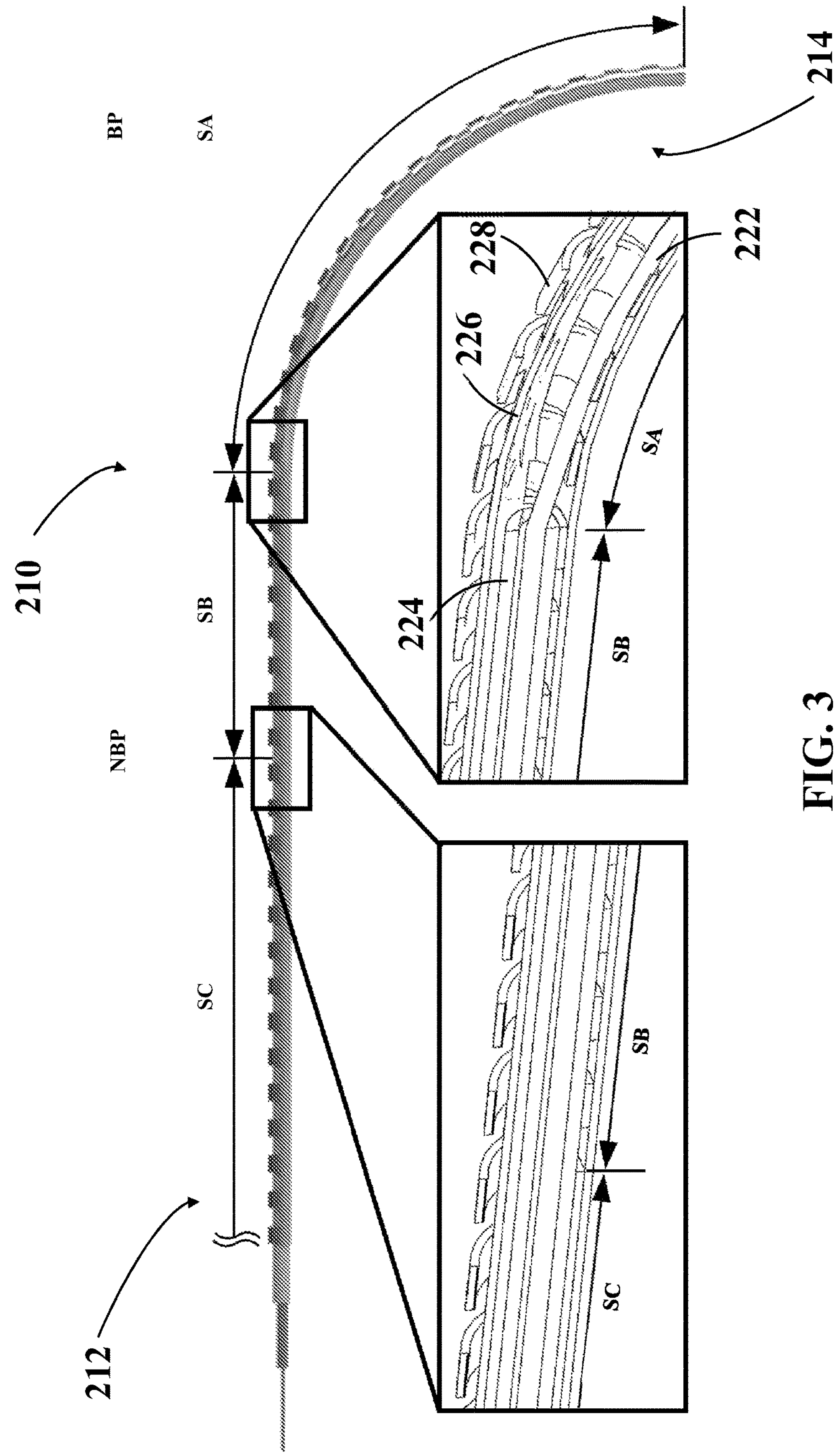
FIG. 3 is a schematic illustrating the segments and portions of the path-providing guide, according to an exemplary embodiment.

As shown in FIGS. 2-3, a robotically steerable guidewire system 200 can comprise a path-providing guide 210 comprising a proximal portion 212 and a distal portion 214, the path-providing guide 210 configured to locate a distal end of a guidewire to a destination. The path-providing guide 210 has an operable length that hereinafter may be described as the combined lengths of consecutive segments lengths of Segment A (SA), Segment B (SB), and Segment C (SC). The operable length of the path-providing guide 210 may also be described as the combined lengths of consecutive segments lengths of a Non-Bending Portion (NBP) and a Bending Portion (BP).

A control unit/actuation module 300 is operably connected to the path-providing guide 210. The path-providing guide 210 and control unit 300 are cooperatively configured to simultaneously and independently control the (an amount of) curvature K of the distal portion BP of the path-providing guide 210, and control an available length SA of bending of the distal portion BP of the path-providing guide 210.

The path-providing guide 210 comprises a coaxial arrangement of tubular elements 220 and a tendon 222 connected to one of the tubular elements. As used herein, being "coaxial" and/or "coaxially aligned" are relative terms and does not require an idealized perfect axial alignment of elements. The present invention is operable over a range of alignments that facilitate telescoping abilities, including a "nested" arrangement of tubular elements.

It will also be understood by those of skill in the art that the terms "stiffness" and/or having the quality of being stiff/rigid can also be described using other relative terms, like "compliant" and/or having the quality of being compliant/flexible. These relative terms can describe a component of the present invention from different directions, for example, a component or portion of a component having an increase in stiffness along a length, or a decrease in compliance. Or be more compliant, meaning having less stiffness.

The control unit 300 is configured to control (i) the relative axial alignment of the tubular elements 220, and/or (ii) how one another tubular element is centrically aligned within another tubular element, and/or (iii) control the relative lateral alignment of the tubular elements 220, and/or (iv) the telescoping arrangement or lateral displacement of one tubular element related to another tubular element, and/or (v) control the relative rotational alignment of the tubular elements 220, and/or (vi) control a stroke of the tendon 222.

The control of the relative axial alignment of the tubular elements 220 is dependent on the snugness of fit of one within another. For example, if the tolerance between an outer wall of an innermost tubular element and the inner wall of a next tubular element is negligible, then the amount "off-center" the innermost tubular element can be is negligible. Alternatively, if the difference between diameters of the tubular element (should that be equally ovate in cross-section), the more tolerance there is to have the relative axial alignment of the tubular elements away from a common axis of rotation.

The control the relative lateral alignment of the tubular elements 220 is less dependent upon the above tolerances. As long as one tubular element can "slide" relative to another, then the length that one might extend or retract relative to another is fairly easily controllable.

The control the relative rotational alignment of the tubular elements 220 enable fine-tuning of stiffness of the distal portion(s) of the path-providing guide 210 and enable the guidewire to travel out of plane (in three-dimensions).

The control of the relative rotational alignment of the tubular elements 220 is relevant when the outer/inner geometries of the tubular elements are different. For example, if the innermost tubular element has a uniformly circular cross-section along its length, with a uniform wall thickness and composed of the same materials throughout, and if the next tubular element has a uniformly circular cross-section along its length large enough to accommodate the innermost tubular element therethrough, and has a uniform wall thickness and is composed of the same materials throughout, then the relative rotational alignment between the tubular elements is unaffected by rotation of any one tubular element. They are effectively featureless as to rotational conditions one to the other.

However, if one tubular element has a set of features that do not possesses rotational symmetry, then how much one tubular element is rotated relative to another will affect the relationship between the tubular elements.

In an exemplary embodiment, at least one tubular element 220 has stiffness features that enable the stiffness of the proximal portion NBP of the path-providing guide 210 is greater than the stiffness of the distal portion BP of the path-providing guide 220.

The tubular elements 220 can comprises an inner tubular element 224 with an inner channel, an intermediate tubular element 226 having a stiffness feature 232 along at least a portion of the length of the intermediate tubular element 226, and an outer tubular element 228 having a stiffness feature 234 along at least a portion of the length of the outer tubular element 228.

The tubular elements 224, 226, 228 each have suitable cross-sectional dimensions such that a guidewire is rotationally and laterally displaceable within the inner channel of the inner tubular element 224, the inner tubular element 224 is rotationally and laterally displaceable within the intermediate tubular element 226, and the intermediate tubular element 226 is rotationally and laterally displaceable within the outer tubular element 228.

The intermediate tubular element 226 has a length defined from a proximal end to a distal end, and the stiffness feature 232 can comprise a set of notches 242 that begin at an intermediate location (the proximal end of SB) of the intermediate tubular element 226 and extend to the distal end (the distal end of SA) of the intermediate tubular element 226.

The outer tubular element 228 has a length defined from a proximal end to a distal end, and the stiffness feature 234 can comprise a set of notches 244 that begin at an intermediate location (the proximal end of SC) of the outer tubular element 228 and extend to the distal end (the distal end of SA) of the outer tubular element 228.

The length of the set of notches 244 of the outer tubular element 228 as shown is greater than the length of the set of notches 242 of the intermediate tubular element 226, although the lengths of the set(s) of notches can vary.

The set of notches 244 of the outer tubular element 228 preferably has a phase difference from the set of notches 242 of the intermediate tubular element 226 enabling the intermediate tubular element 226 to be operationally rotational and laterally displaceable within/without the outer tubular element 228. The phase difference of the sets of notches is preferably, but not necessarily, 180°.

Either or both sets of notches 242, 244, can form a variety of notch geometries/patterns, for example, unidirectional asymmetric notch joints of the intermediate tubular element 226 and the outer tubular element 228.

With control of the tendon 222, the telescoping of tubular elements 224, 226, 228, the relative rotational alignment of the stiffness features 232, 234, and the overall displacement of the system 200 define both the reach of a guidewire, and the ability of the guidewire to navigate arcuate paths, for example, vasculature systems. The system 200 generally embodies the inventive snaking ability by altering the stiffness of portions of the path-providing guide 210.

It will be understood by those of skill in the art that the present invention can comprise more than one tendon, and more than three tubular elements, which additional components can extend the range and ability of following a tortuous path.

Further, it will be understood by those of skill in the art that none, some or all of the tubular elements can have a similar cross-sectional profile from one another, and indeed even a single tubular element need not be uniformly cross-sectional along its length. Tubular elements can slide within/without one another, and rotate inside or outside one another, with varying cross-sectional shapes, one tubular element from another, and with varying cross-sectional shapes and/or dimensions over a length of a single tubular element.

The stiffness of the portion SC of the path-providing guide 210 is greater than the stiffness of the portion SB of the path-providing guide 210. The stiffness of the portion SB of the path-providing guide 210 is greater than the stiffness of the portion SA of the path-providing guide 210.

The stiffness of each portion of the path-providing guide 210 is controllable by the relative axial alignment of the tubular elements 220, the relative lateral alignment of the tubular elements 220, the relative rotational alignment of the tubular elements 226, 228, and the stroke of the tendon 222, such that the portion SC of the path-providing guide 210 is a length of the path-providing guide comprising the coaxial arrangement of a first portion of inner tubular element 224, a first portion of the intermediate tubular element 226 (that is without the set of notches), and a first portion of the outer tubular element 228 (that is with the set of notches 244).

The portion SB of the path-providing guide 210 is a length of the path-providing guide 210 comprising the coaxial arrangement of a second portion of the inner tubular element 224, a second portion of the intermediate tubular element 226 (that is with the set of notches 242), and a second portion of the outer tubular element 228 (that is with the set of notches 244), wherein the first portion and the second portion of the inner tubular element 224 comprise the full length of the inner tubular element 224.

The BP portion of the path-providing guide 210 is a length of the path-providing guide 210 comprising the coaxial arrangement of a third portion of the intermediate tubular element 226 (that is with the set of notches 242), and a third portion of the outer tubular element 228 (that is with the set of notches 244).

The coaxial tubular elements 220 enables the present invention to implement the 'follow-the-leader' motion with limited DoFs in the compact space required for a guidewire. In an exemplary embodiment, the inner tubular element 224 is made of stainless-steel and has a regular cylindrical cross-section with an inner channel. In an exemplary embodiment, the intermediate and outer tubular elements 226, 228 are Nitinol tubes with notch patterns micromachined along at least a portion of the lengths of each tube.

Each of tubular elements has suitable dimensions so that they can respectively slide within each other. To avoid collision/interference between the notches on the intermediate and outer tubular element, there is a 180° phase difference in the notches. The tendon 222 passes through the inner tubular element 224 and is connected to the distal end of the intermediate tubular element 226.

Depending on the relative positions of each tubular element and notch pattern, in SA, the notch pattern on the intermediate tubular element decreases its second moment of area and shifts its neutral axis to the un-notched side, which increases compliance as well as the moment arm of the tendon of this segment. In SB, however, introducing the stainless-steel inner tubular element increases the second moment of area of the combined structure, resulting in a significant increase in the stiffness of as well as decrease of the moment arm of this segment. Lastly, only the outer tubular element 228 retains its notch patterns in SC, which contributes to an increased stiffness of this segment.

Therefore, the present invention as shown has three segments with varying stiffness and can be largely classified into bending portion BP (i.e., SA) and non-bending portions NBP (i.e., SB and SC) depending on the relative position of the inner tubular element 224.

Referring to FIG. 2, the control unit/actuation module 300 drives the path-providing guide 210. The tendon 222 and inner and outer tubular elements 224, 228 are connected to drives 302, 304, 312, respectively. In an exemplary embodiment, these drives are linear motors.

It will be understood by those of skill in the art that not only the motors, but all elements of the present invention can be chosen for a particular modality of use. For example, if the present invention is used in a magnetic resonance imaging (MRI) environment, the motors, tubular elements and tendon should avoid those materials detrimental in an MRI environment.

Adaptability of the present invention is further enhanced with selection of the types of components selected. While linear motors can be used, so too can many others of displacement mechanism, including piezo-electric motors and rack and pinons. Further, while stainless-steel was useful for the inner tubular element, other materials can be used to provide the present invention with the beneficial flexibility/stiffness disclosed herein. Further, while Nitinol was useful for the intermediate and outer tubular elements, other materials sufficiently elastic and yet stiff to embody stiff features—like notches—are known.

The intermediate tubular element 226 can be fixed to the control unit/actuation module 300 itself or be rotationally driven by drive 308/gear 314 assembly that can impart rotation of the intermediate tubular element 226. It will be understood by those of skill in the art that the operative consideration is the relative rotation of the intermediate tubular element 226 and the outer tubular element 228. Thus, in alternative arrangements, the outer tubular element 228 can be rotationally controlled with the intermediate tubular element 226 having a fixed rotation, or both elements 226, 228 can have rotational control.

As shown, the actuation module has five control variables: $X_1$, $X_2$, $X_3$, $X_4$ and $\psi$, corresponding to tendon stroke, relative distance between the inner and tubular elements, displacement of the outer tubular element, displacement of the actuation module, and rotation of the intermediate tubular element, respectively.

Figures 4A, 4B, 4C:
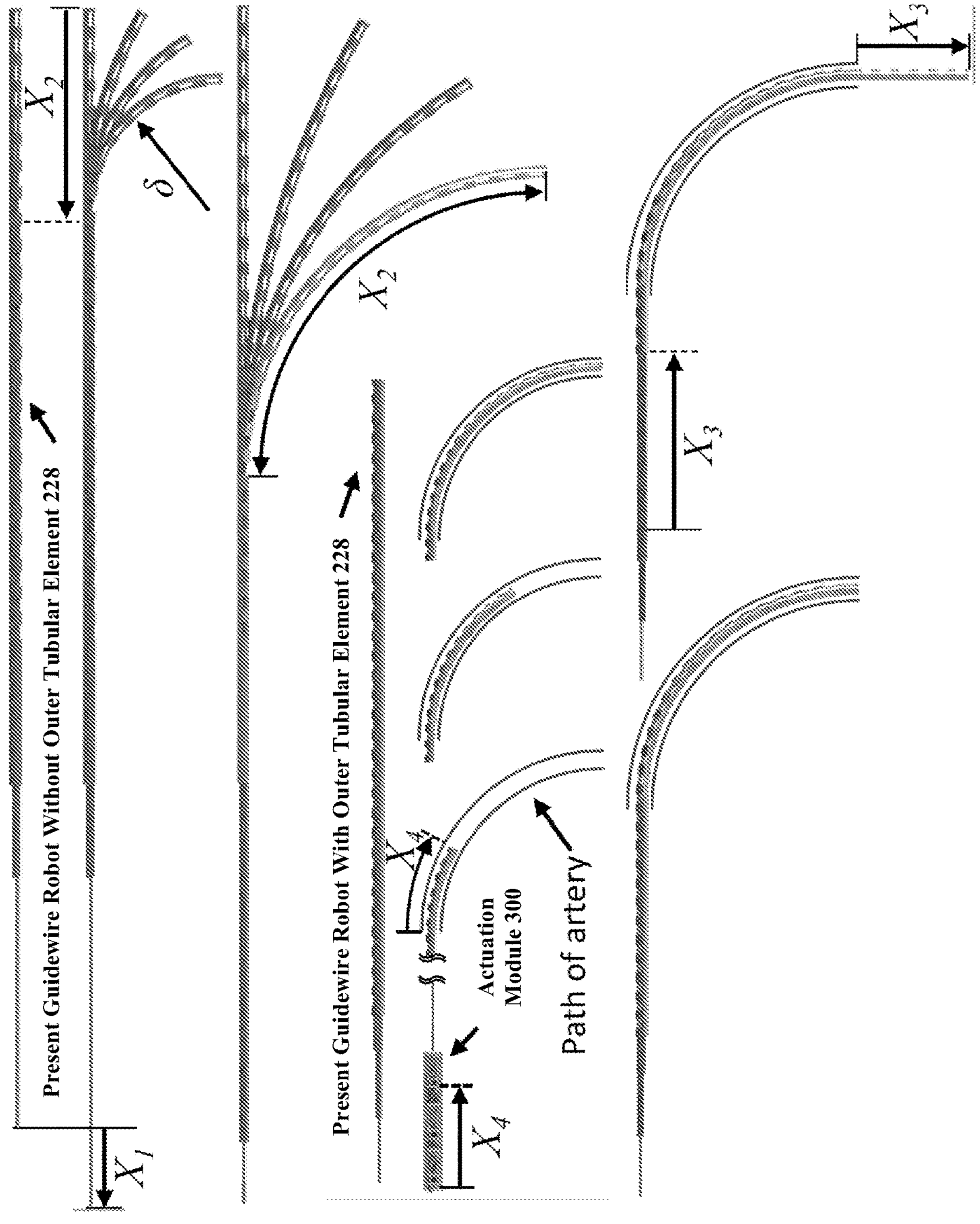
FIG. 4A illustrates controlling the tendon stroke $X_1$ and joint length $X_2$ allows for variable curvature.
FIG. 4B illustrates controlling $X_1$ and $X_2$ while advancing the actuation module $X_4$ allows for follow-the-leader motion.
FIG. 4C illustrates advancing outer tubular element individually $X_3$ to go further into a target vasculature, while retaining the curvature at the location of the vessel tortuosity.

Given the control variables, the present invention can form the shape of any arc within geometric constraints, since $X_1$ and $X_2$ control the curvature and arc length of the distal portion of the path-providing guide 210 (bending segment A), respectively (see FIG. 4A). Therefore, the bending segment A can follow the curved path of the vasculature, which is a function of the curvature and arc length by controlling $X_1$ and $X_2$, as well as feeding the actuation module $X_4$, which leads to a follow-the-leader motion during guidance along a curved path (see FIG. 4B) without passive support from the vasculature wall.

The outer tubular element 228 can slide and proceed further along the curved intermediate tubular element 226 (see FIG. 4C). The intermediate tubular element 226 can provide a stable passage for the outer tubular element 228 to reach proper locations as an introducer sheath, while retaining the curvature at the location of the curved path. This entire procedure can then be repeated at a next curved path, until the final target location is reached. The present invention therefore provides easy insertion of the guidewire into tortuous vasculature without replacement of guidewire, thereby significantly reducing the procedure time.

Figures 5A, 5B:
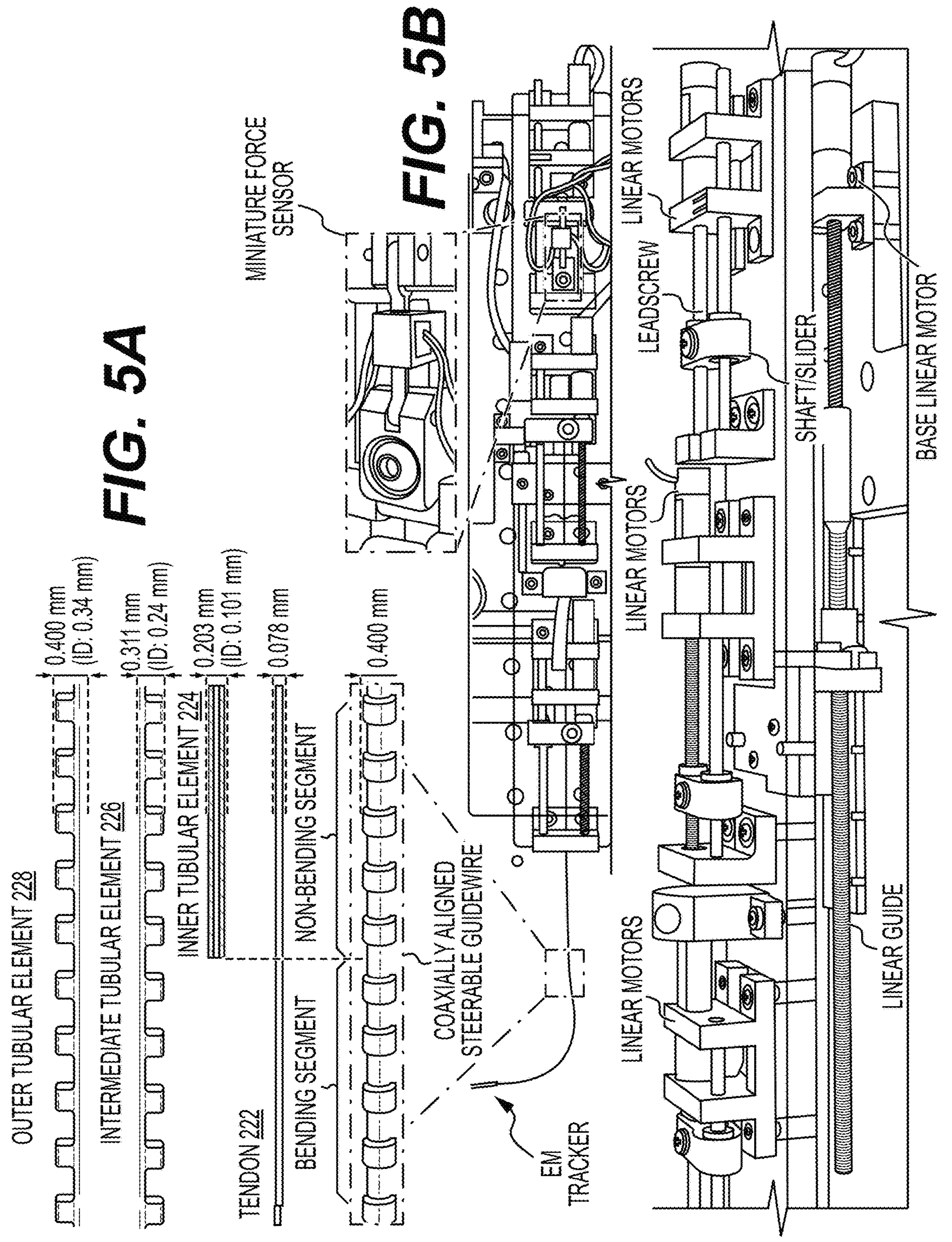
FIG. 5A illustrates coaxial tubes and dimensions according to an exemplary embodiment.
FIG. 5B illustrates the actuation stage showing individual linear motors to control the guidewire according to an exemplary embodiment.
Figure 6A:
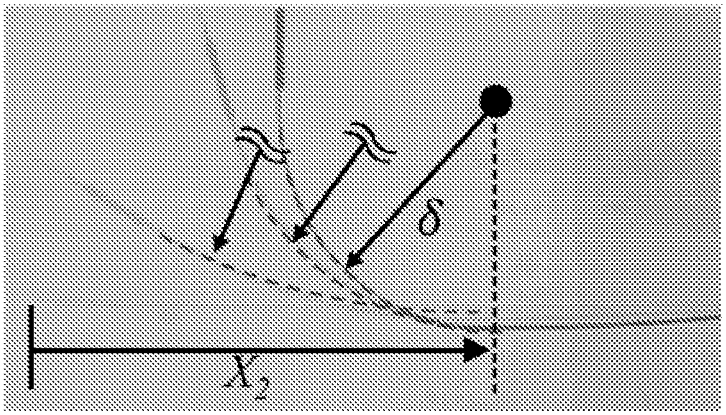
FIGS. 6A-6C present demonstrations of the present invention according to an exemplary embodiment achieving various curvatures at different arc lengths $X_2$.
Figure 6B:
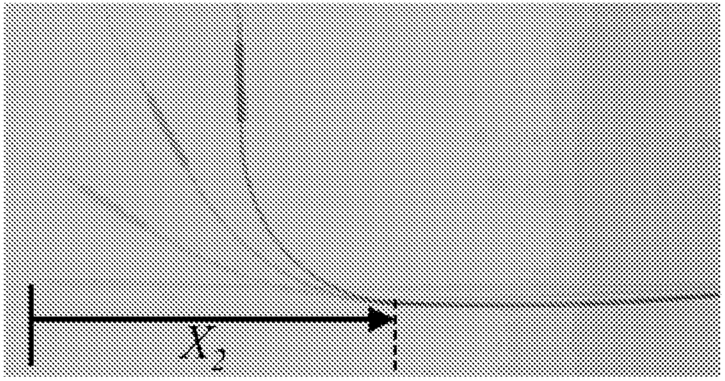
Figure 6C:
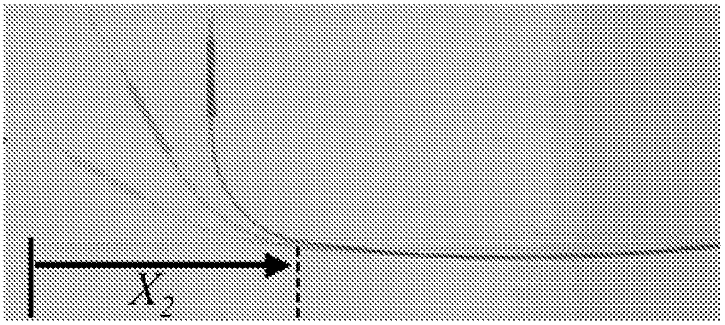

A prototype of the present invention was constructed and assembled as shown in FIG. 5B. The intermediate and outer tubular elements 226, 228 are made using superelastic Nitinol for high bending capability and their notch patterns are fabricated on a femtosecond laser (WS-Flex Ultra-Short Pulse Laser Workstation, Optec, Frameries, Belgium). The tendon 222 is also made of Nitinol for ease of insertion through the tubular elements and ease of attachment. Finally, the inner tubular element 224 is stainless-steel since it has a higher stiffness than the intermediate and outer tubular elements. The outer tubular element 228, the inner tubular element 224, and the tendon 222 are connected to linear motors (Maxon Precision Motors, MA, United States, resolution≈2.8 μm) and generate linear motion, sliding on each surface (see FIG. 5B). Through the motor strokes, the tendon displacement $X_1$ can be controlled and the arc length of SA $X_2$, thereby achieving variable curvatures at several arc lengths of SA (see FIGS. 6A, 6B, 6C). The entire actuation stage 300 is installed on the base stage with a linear guide and actuated by a base linear motor 306 (to control $X_4$). The tendon 222 is connected to a miniature force sensor to measure the tendon tension. The dimensions of the tubular elements shown in FIG. 5A used in the prototype are summarized in TABLE I.

TABLE I

| Items | Outer Tube | Intermediate Tube | Inner Tube | Tendon |
|---|---|---|---|---|
| Total Length (mm) | 188.4 | 240.0 | 256.6 | 280.0 |
| Length of Notched Section (mm) | 94.0 | 57.0 | | |
| Outer Diameter, $2r_o$ (mm) | 0.400 | 0.311 | 0.203 | 0.078 |
| Inner Diameter, $2r_i$ (mm) | 0.340 | 0.240 | 0.102 | |
| d (mm) | 0.270 | 0.249 | | |
| h (mm) | 0.3 | 0.3 | | |
| c (mm) | 0.3 | 0.3 | | |
| Young's Modulus (GPa) | 77.3 | 77.3 | 200 | 53.965 |

| Items | $l_0$ | $l_1$ | $l_2$ | $l_3$ | $l_4$ |
|---|---|---|---|---|---|
| Dimension (mm) | 136.9 | 14.0 | 89.1 | 16.5 | 92.6 |

In tested embodiments, the system was fabricated with a short length ($l_0$) different than that of conventional guidewires for in vitro feasibility tests.

Figure 7:
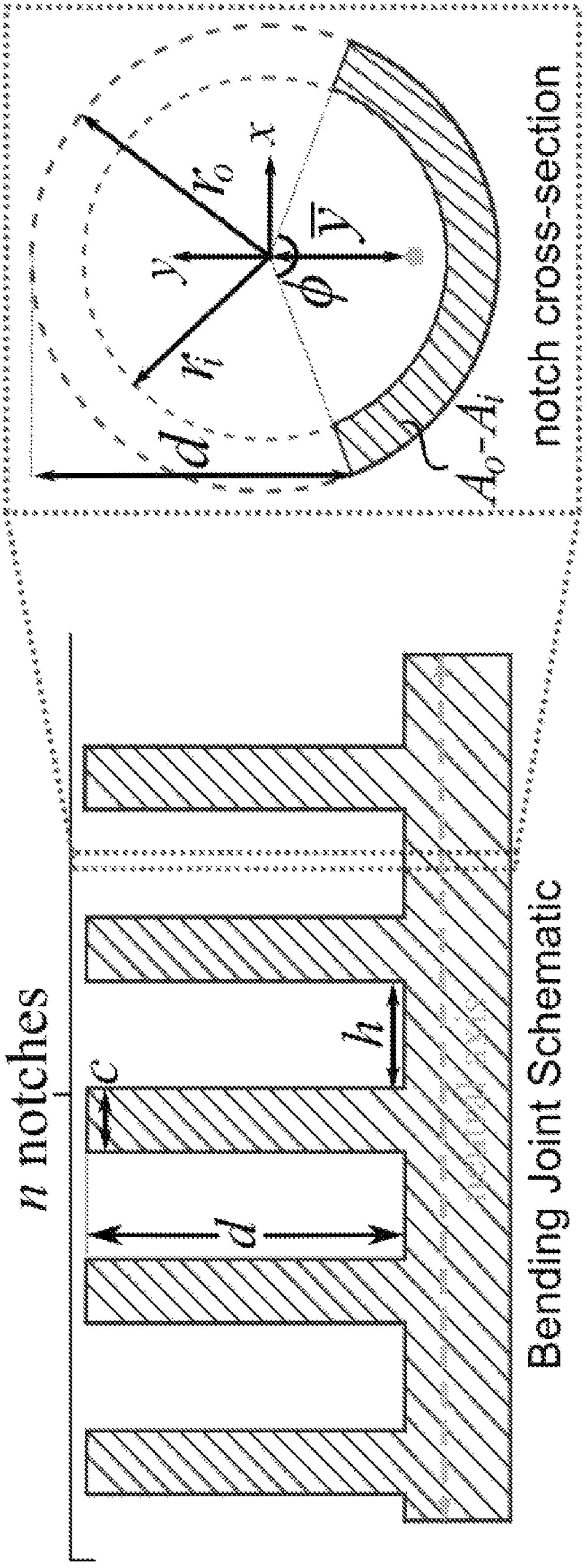
FIG. 7 illustrates a bending joint schematic and notch cross-section view, according to an exemplary embodiment.

To derive the relationship between the tendon stroke $X_1$, the desired curvature K, and arc length of SA $X_2$, and to derive a static model for the bending portion BP of the guidewire and a model for the coupling in non-bending portions NBPs, consider the case of a single notched tubular element ("tube") with notch depth, d, notch width, h, and n notches in the joint (see FIG. 7). Furthermore, $r_o$ and $r_i$ are the outer and inner radii of the tube respectively and laser micromachining creates a cross-section of area $A_o$-$A_i$ at the notches (see FIG. 7 (inset)).

This cross-section is expressed as a sector of area, $$A_i = \frac{\phi r_i^2}{2}$$

subtracted from a sector of area, $$A_o = \frac{\phi r_o^2}{2} \text{ where } \phi = 2\arccos\left(\frac{d - r_o}{r_o}\right)$$

is the central angle created by laser micromachining. To derive the kinematics of joint, an expression for the neutral axis of the joint must first be arrived. As can be seen in FIG. 7, the neutral axis of the joint is shifted away from the central axis of the tube along the y-axis, due to the notch pattern. The location of this axis for the outer circular sector with area, $A_o$, is given as $$\bar{y}_o = \frac{4r_o\left(\sin\left(\frac{\phi}{2}\right)\right)}{3\phi},$$

and for the inner circular sector with area, $A_i$, it is given as $$\bar{y}_i = \frac{4r_i\left(\sin\left(\frac{\phi}{2}\right)\right)}{3\phi}.$$

Finally, the neutral axis of a composite structure such as the notch cross-section with area, $A_o$-$A_i$ is given as follows:

$$\bar{y}_i = \frac{A_o\bar{y}_o - A_i\bar{y}_i}{A_o - A_i} \quad (1)$$

Therefore, the location of the neutral axis of the present tube is given as follows (where subscript "j" refers to the outer, intermediate, or inner tubular element):

$$\bar{y}_j(d, r_o, r_i) = \frac{4\sin\left(\frac{\phi}{2}\right)\left(r_o^3 - r_i^3\right)}{3\phi\left(r_o^2 - r_i^2\right)} \quad (2)$$

The second moment of area of the notched segment of area $A_o$-$A_i$ is given as follows:

$$I_{xx} = \left(\frac{\phi + \sin\phi}{8}\right)\left(r_o^4 - r_i^4\right) \quad (3)$$

Now, from the parallel axis theorem and Equation (2), the second moment of area of the notched segment about the neutral axis of the tube is given by:

$$I_j(d, r_o, r_i) = \left(r_o^4 - r_i^4\right)\left(\frac{\phi + \sin\phi}{8}\right) - \frac{8\sin^2\left(\frac{\phi}{2}\right)\left(r_o^3 - r_i^3\right)^2}{9\phi\left(r_o^2 - r_i^2\right)} \quad (4)$$

Figure 8:
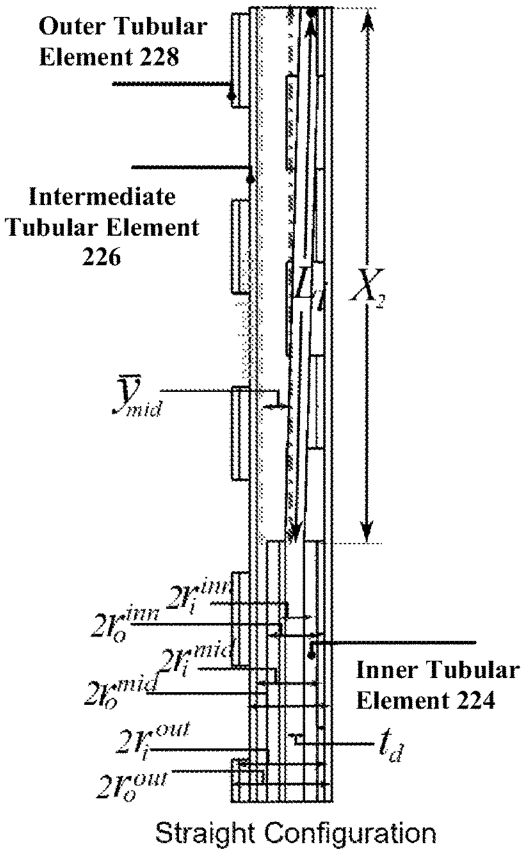
FIGS. 8-9 illustrate the coaxial tube structure geometry in the straight configuration (FIG. 8) and with curvature $$\kappa = \frac{1}{\delta}$$

Given a desired curvature, K, and the joint length, $X_2$, the bending angle required is given by $\theta=\kappa X_2$. A schematic of the bending portion of the robot along with the various lengths and radii of the tubes is shown in FIG. 8. The tendon diameter is indicated as $t_d$. The initial length of the tendon in this straight configuration is given by $$L_i(X_2) = \sqrt{r_{off}^2 - X_2^2}. \text{ Here, } r_{off} = r_o^{inn} - r_i^{inn}$$

is the offset between the inner tube and the intermediate notch joint. This is the length at which the joint begins to bend and is therefore critical to eliminate any slacking of the tendon at any stage.

Figure 9:
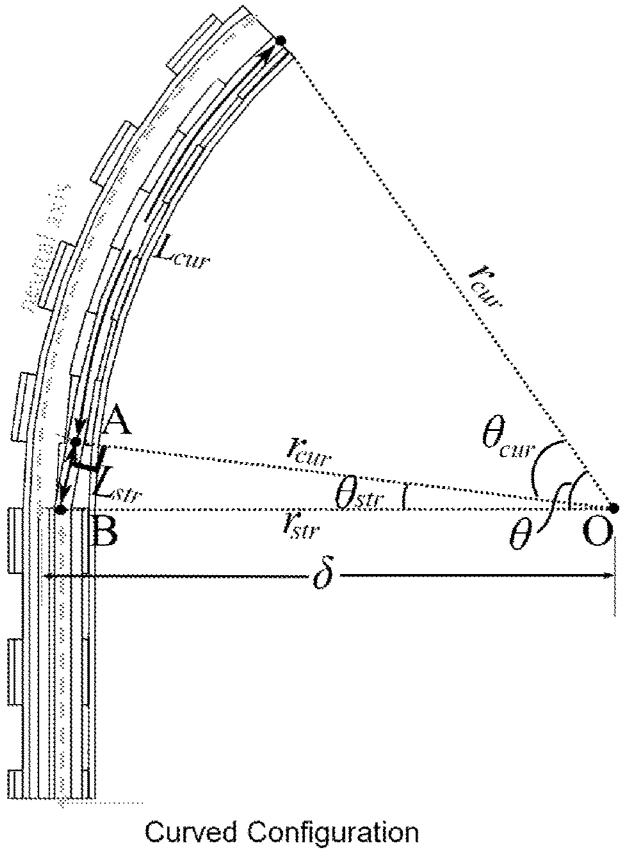

As the bending segment SA of the guidewire bends to a certain curvature K, the inner wall of the intermediate tube forms an arc of angle θ with center 'O' (see FIG. 9). As a result, the path of the tendon through the intermediate tube can be divided into two portions. The straight portion of the tendon, denoted by line segment $\overline{AB}$ in FIG. 9, runs from the inner wall of the inner tube and intersects the bending portion of the intermediate tube at point 'A' such that the line $\overline{AB}$ is tangential to the bending curve at point 'A'.

The second portion, denoted by arc $\widehat{(AC)}$ in FIG. 9, bends with the intermediate tube, running along the inner wall of the intermediate tube with radius, $r_{cur}$. Furthermore, $$\bar{y}_{mid}\left(d^{mid}, r_o^{mid}, r_i^{mid}\right)$$

(derived in Equation (2) and abbreviated as $\bar{y}_{mid}$ in following references) is the location of the neutral axis of the notched section of the intermediate tube in its central coordinate frame. From geometry, the triangle formed by the straight portion of the tendon, ΔOAB, is a right angled triangle, where $$\overline{OA} = r_{cur} = \left(\delta - \overline{y}_{mid} - r_i^{mid} + r_t\right).$$

and $$\overline{OB} = r_{str} = \left(\delta - \overline{y}_{mid} - r_i^{mid} + r_o^{inn} - r_i^{inn} + r_t\right)$$

Furthermore, $$\delta = \frac{1}{\kappa}$$

is the radius of curvature of the intermediate joint and $r_t = t_d/2 = 0.038$ mm is the radius of the tendon cross-section.

The length of the straight portion of the tendon is then given as $$L_{str} = \sqrt{r_{str}^2 - r_{cur}^2}.$$

The interior angle $\theta_{str}$ between the sides $\overline{OA}$ and $\overline{OB}$ is given as $\theta_{str} = \arccos(r_{cur}/r_{str})$ and the length of the curved portion of the tendon is $L_{cur} = r_{cur}(\theta - \theta_{str})$ Finally, the tendon displacement needed for the target geometry combination of κ, $X_2$ is given by $\Delta L^{kin}(\kappa, X_2) = L_i(X_2) - (L_{str} + L_{cur})$. Furthermore, motor stroke, $X_1$, is highly dominated by tendon elongation for any κ, $X_2$ combination. Therefore, an elongation term is added to the kinematics model as follows:

$$X_1 = \Delta L^{kin}(\kappa, X_2) + \frac{F_t L_{total}}{\pi E_t r_t^2} \quad (5)$$

Figure 10:
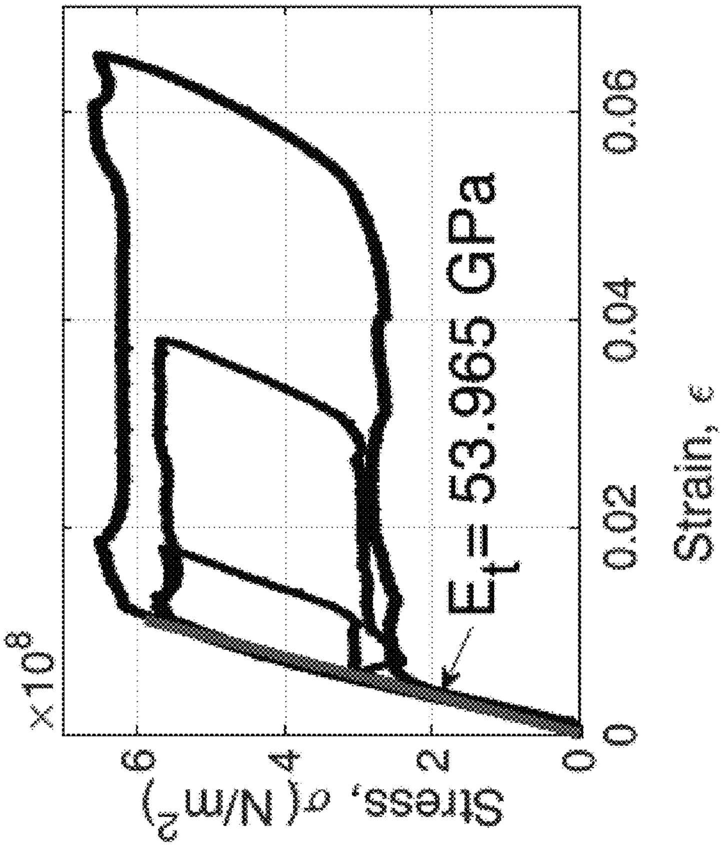
FIG. 10 is a graph of stress-strain curves for the Nitinol tendon.
Figure 11:
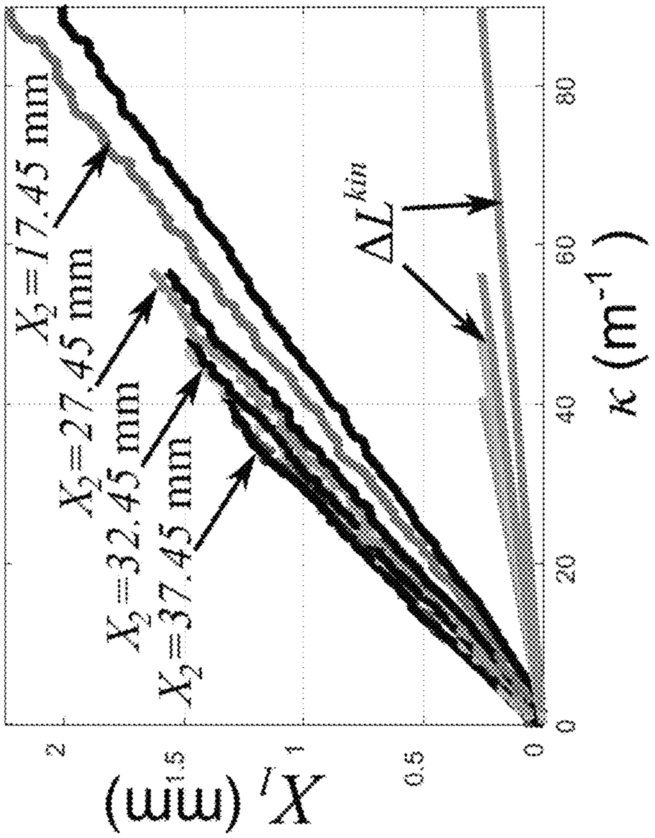
FIG. 11 is a graph of the $\kappa$-$X_1$ relationship as described hereinafter for several values of $X_2$.

Here, the applied tendon tension is $F_t$ and $L_{total} = 337.2$ mm is the "un-elongated" original length of the entire tendon from the tip of the robot to the actuator. $E_t = 53.965$ GPa is Young's modulus of the Nitinol tendon in its austenite phase and was experimentally derived (see FIG. 10). To test the used kinematics model, $\kappa - X_1$ is evaluated for several joint length, $X_2$, values (see FIG. 11).

For each experiment, the tendon tension, $F_t$, was used to evaluate and account for tendon elongation. Motor stroke data from the encoder was used as the ground truth for each case. Finally, for each case, the kinematics term, $\Delta L^{kin}$, is also plotted. In each case, the tendon elongation dominates the joint kinematics. Furthermore, Equation (5) correctly predicts the joint kinematics, especially for higher values of $X_2$ ($X_2$={37.45 mm, 32.45 mm, 27.45 mm} in FIG. 11, RMSE=0.0324 mm). The higher deviation from the model at lower $X_2$ values ($X_2$=17.45 mm in FIG. 11, RMSE=0.1331 mm) is believed due to higher friction losses as the joint stiffens with decreasing joint length.

Ideally, the design goal is that a tendon stroke of $X_1$ will result in a curvature, K in the bending segment A (see SA in FIGS. 2-3), while the non-bending segments B, C (see SB and SC in FIGS. 2-3) will not undergo any deformation. However, due to the arrangement of the coaxial tubes within the non-bending segment and the coupling between segments, these segments also undergo a small amount of deformation.

Figure 12:
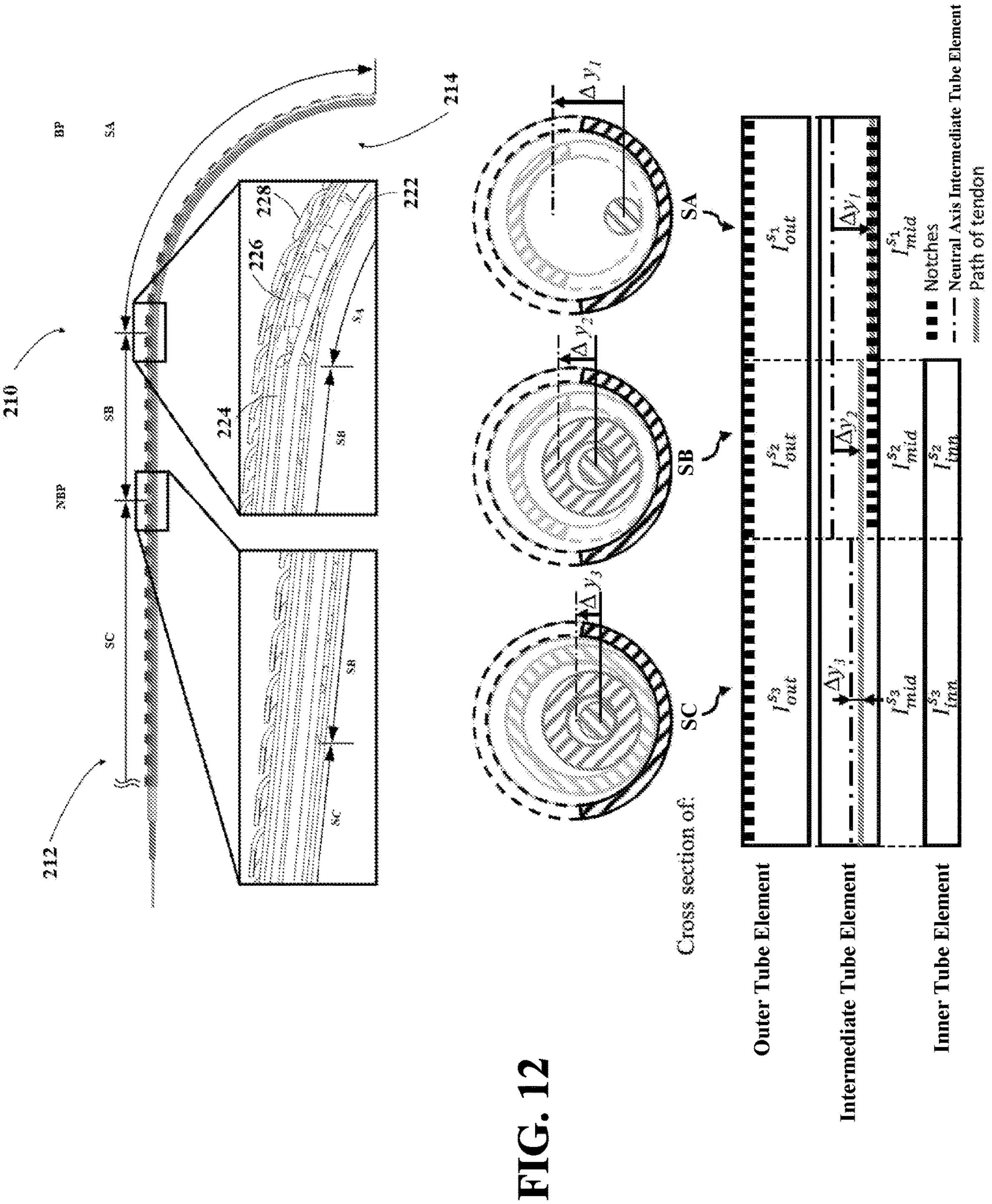
FIG. 12 illustrates cross-sections of the three segments of the present robot according to an exemplary embodiment, with a schematic of each segment with inertia values.

A statics model for SA and a coupling model relating joint notch depths and coupling effects on the non-bending segments is developed and validated. SA (see inset in FIG. 12) is composed of the intermediate and outer notched tubes, actuated by the tendon placed along the inner wall of the intermediate tube. Since the tendon is connected to the distal tip of the intermediate tube, a moment, $\Delta M = F_t \Delta y_n$, is applied to the entire structure. Here, the moment arm, $\Delta y_n$, is the displacement between the tendon and neutral axis of the intermediate tube in segment-n (see SA, SB, SC in FIG. 12). Furthermore, due to the actuation of the tendon, the intermediate tube gets displaced and touches the outer tube (see the cross-section of the SB in FIG. 12). The moment arm of the tendon tension, $$\Delta y_n = \overline{y}_{mid} + r_i^{mid} - r_t,$$

still remains constant. The bending of any of the notched tubes (intermediate or outer) is believed to occur due to the accumulation of the bending segments at every notch along the tube.

Since the number of notches in each joint is high (n={95, 160} for the intermediate and outer tubes respectively), for a single notched element of a tube, the curvature achieved by the bending element may therefore be considered negligible (≤2° for a 180° bend in the joint). Furthermore, the total bending angle is assumed to be distributed uniformly across all the notches, while the segment of length, c (see FIG. 7), between two notches does not undergo any bending.

Assuming uniform notch spacing within a certain segment, β=h/(h+c)' is defined to indicate the ratio of the width of an individual notch to the sum of notched and un-notched individual section of the joint. The notched and un-notched sections are uniformly repeated for the specific joint segment. Note that the intermediate and outer tube were designed with a same value of c. By applying the Euler beam equation for the $\kappa - F_t$ relationship for the SA, the following is obtained:

$$F_t = \frac{E\left(I_{out}^{s1} + I_{mid}^{s1}\right)\kappa}{\beta \Delta y_1} \quad (6)$$

Since the two tubes are not bonded together and can slide over each other, the resulting curvature, K, occurs due to the sum of inertial terms in the above equation. In the Equation (6), a second moment of area of each tube for the SA, $$I_j^{s1} = I_j\left(d_j, r_o^j, r_i^j\right),$$

where j={out, mid} is defined in Equation (4). For SB, the tendon is no longer located at the inner wall of the intermediate tube but is located inside the inner tube (as seen in the cross-section view in FIG. 12). This reduces the moment arm of the applied tendon tension to $$\Delta y_2 = \Delta y_1 - \left(r_o^{inn} - r_i^{inn}\right).$$

Furthermore, the addition of the inner tube in SB adds an inertia term in the statics model (see FIG. 12):

$$F_t = \frac{\left(E\left(I^{s2}_{out} + I^{s2}_{mid}\right)/\beta + E_{inn}I^{s2}_{inn}\right)\kappa_{s_2}}{\Delta y_2} \tag{7}$$

The inner tube was made of 304 stainless-steel and therefore, it is assumed $E_{inn}$=200 GPa from manufacturer's datasheet. Furthermore, the inner tube is not notched, and therefore $$I^{s2}_{inn} = I_{inn}\left(0, r^o_{inn}, r^i_{inn}\right)$$

from Equation (4). Since tendon tension $F_t$ stays constant throughout the length of the robot, the value of $F_t$ from Equation (6) can be substituted in Equation (7) to get the following coupling ratio between the curvatures of SA, SB (namely $\kappa$ and $\kappa_{s_2}$):

$$\frac{\kappa_{s_2}}{\kappa} = \frac{E\left(I^{s1}_{out} + I^{s1}_{mid}\right)}{E\left(I^{s2}_{out} + I^{s2}_{mid}\right) + \beta E_{inn}I^{s2}_{inn}}\left(\frac{\Delta y_2}{\Delta y_1}\right) \tag{8}$$

Similar to SB, SC is composed of all three tubes. However, the key difference is that in this segment, the intermediate tube is not notched (see FIG. 12). The moment arm of the applied tendon tension is reduced to $\Delta y_3 = \Delta y_2 - \bar{y}_{mid}$ and the coupling relationship between SA and SC is given as follows:

$$\frac{\kappa_{s_3}}{\kappa} = \frac{E\left(I^{s1}_{out} + I^{s1}_{mid}\right)}{E\left(I^{s3}_{out} + \beta I^{s3}_{mid}\right) + \beta E_{inn}I^{s3}_{inn}}\left(\frac{\Delta y_3}{\Delta y_1}\right) \tag{9}$$

Here, $$I^{s3}_{mid} = I_{mid}\left(d_{mid} = 0, r^o_{mid}, r^i_{mid}\right)$$

is the moment of inertia of the un-notched intermediate tube and is defined in Equation (4). From Equations (8) and (9), it is clear that the ratio of coupling between the bending and non-bending segments depends only on the geometry of the cross-section of the segments (and not their relative lengths). Therefore, $(d_{mid}, d_{out})$ are the only two parameters that can affect coupling. A sum of the coupling ratios, $$\kappa_{tot} = \left|\frac{\kappa_{s_2}}{\kappa}\right| + \left|\frac{\kappa_{s_3}}{\kappa}\right|$$

is used as a cost-function for optimization.

Figure 13:
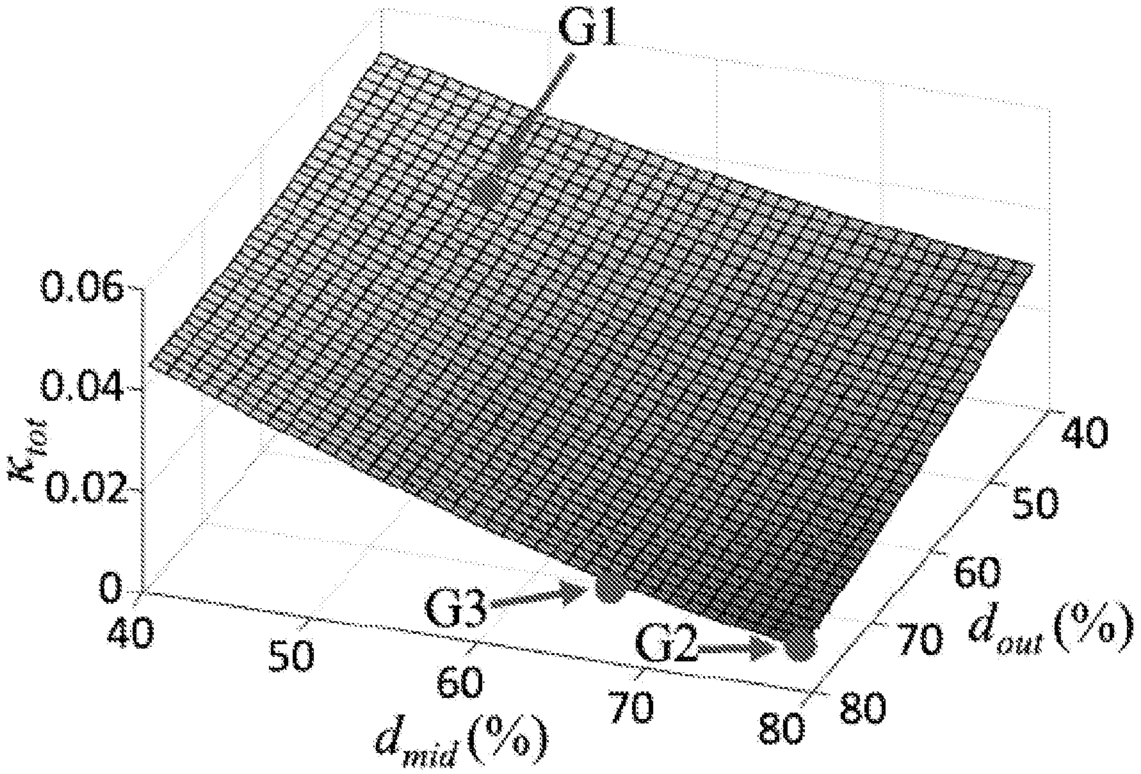
FIG. 13 is a graph illustrating the decoupling estimate, $\kappa_{tot}$ for various intermediate and outer tube depths (in terms of percentage of each tube's outer diameter).

FIG. 13 shows $(d_{mid}, d_{out})$ vs. $\kappa_{tot}$. The parameters $(d_{mid}, d_{out})$ are denoted as a percentage of their corresponding outer diameters. As the depth of the micromachined notch increases, the extent of coupling between segments reduces. However, this decoupling is achieved at the expense of robot tip stiffness.

Figure 15A:
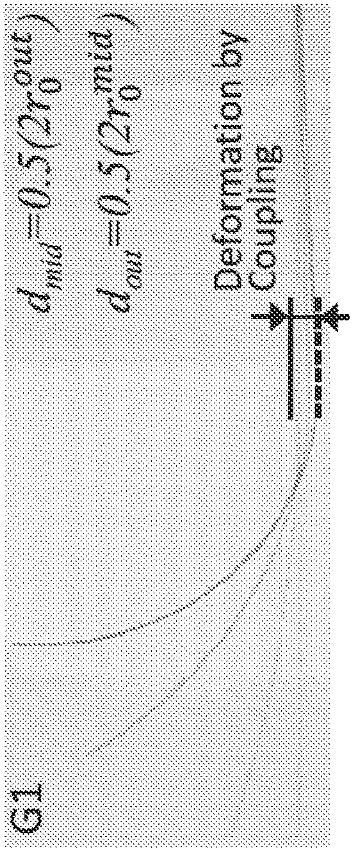
Figure 15B:
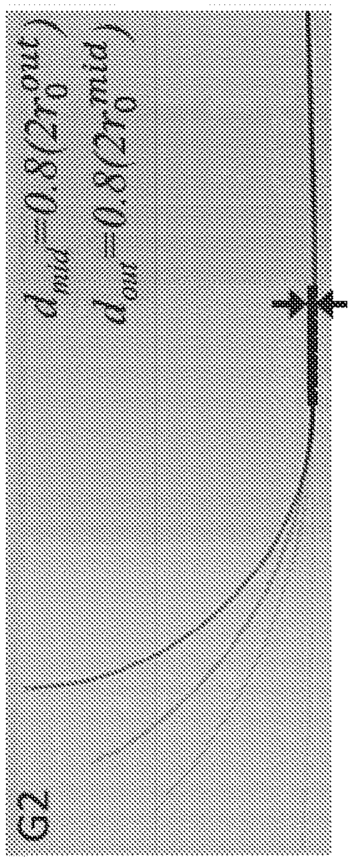
Figure 15A:
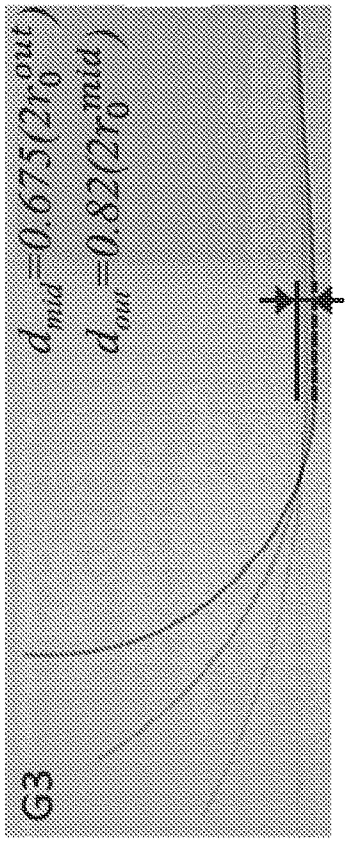

Three samples were micromachined corresponding to varying values of $(d_{mid}, d_{out})$ (see FIGS. 15A, 15B, 15C). As expected, the highest coupling is found in 'G1' (FIG. 15A) and found negligible coupling in 'G2' (FIG. 15B). While joint 'G1' is sufficiently stiff for navigating vasculature but highly coupled, sample 'G2' is extremely compliant and can be used only in cases where a large curvature is required with minimal interaction with the walls of the blood vessels. As a result, the joint 'G3' (FIG. 15B) was chosen as the most likely candidate to achieve high curvatures with minimal coupling and high stiffness.

Figure 14:
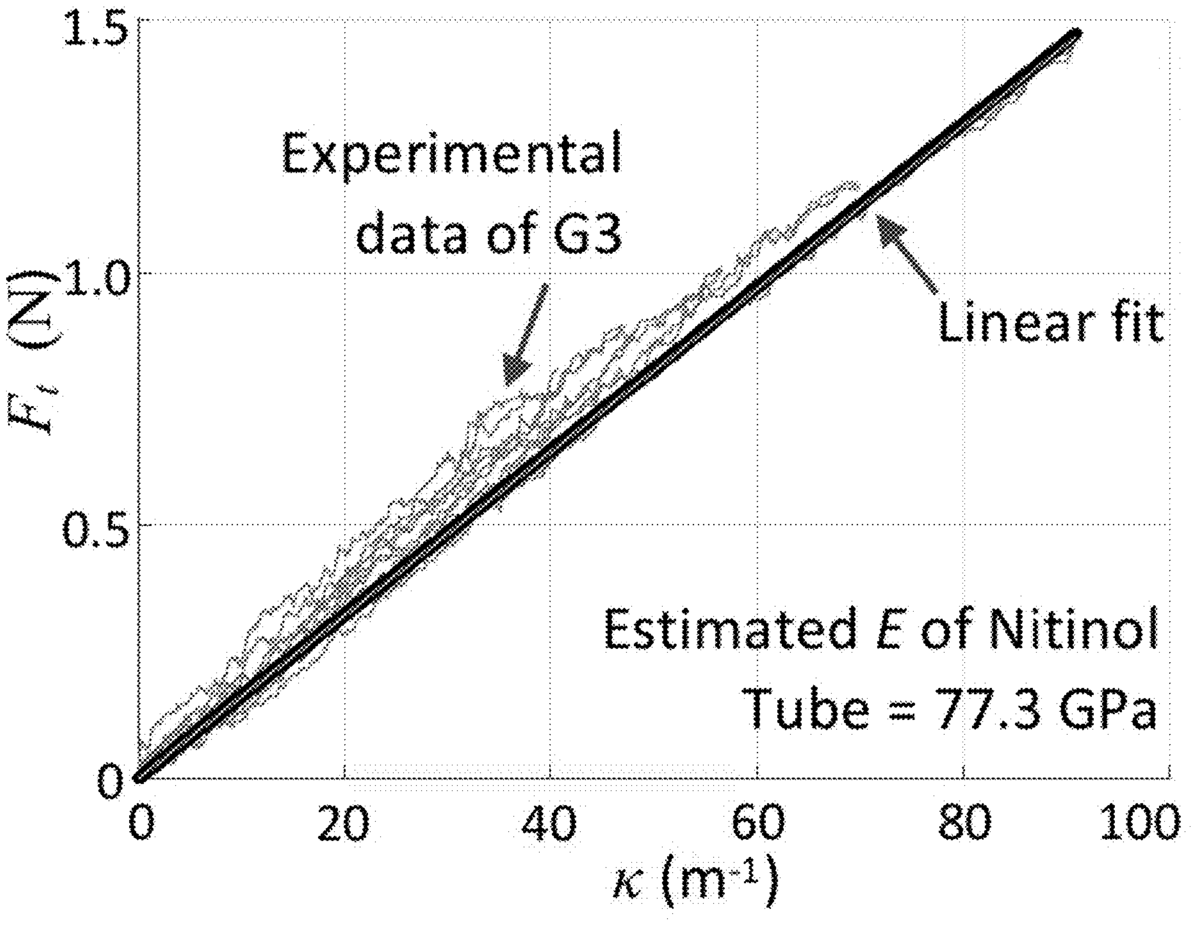
FIG. 14 is a graph illustrating experimental result for the $\kappa$-$F_t$ relationship as described hereinafter.

Next, the statics model for SA was validated (see Equation for sample 'G3'. The prototype of the present invention was actuated so the guidewire could reach several curvatures to obtain a $\kappa$-$F_t$ relationship (see FIG. 14). First, for a variety of curvatures and arc length of SAs ($X_2$={37.45 mm, 32.45 mm, 27.45 mm, 22.45 mm, 17.45 mm}), it is noted that the $\kappa$-$F_t$ relationship stays approximately constant and can be approximated for this geometry by a linear fit (RMSE=0.064 N). Using this linear approximation and Equation (6), and knowing the values for $$\left(I^{s1}_{out} + I^{s1}_{mid}\right)/\beta\Delta y_1$$

from the geometry of sample 'G3,' the elastic modulus of the assembly can be estimated, E=77.3 GPa, which is within the range of valid values for superelastic Nitinol in the austenite phase.

From Equations (5) and (6), a direct relationship between K and $X_1$ is derived with given $X_2$ as follows:

$$X_1 = f(\kappa, X_2) = \Delta L^{kin}(\kappa, X_2) + \frac{E\left(I^{s1}_{out} + I^{s1}_{mid}\right)L_{total}}{\beta\Delta y_1 \pi E_t r_t^2}\kappa \tag{10}$$

Therefore, K can be directly controlled by $X_1$ without the need for any force information.

Figure 16:
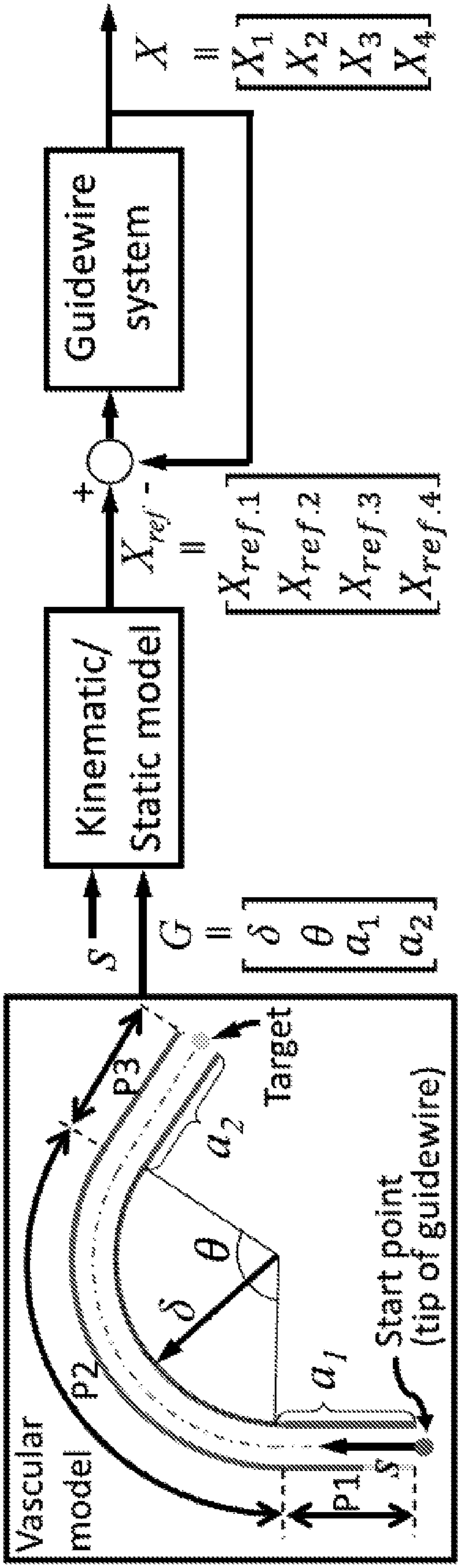
FIG. 16 is a schematic of a control system for the present robot according to an exemplary embodiment.

Based on Equation (10) and the geometric information of the vessel, $G=[\delta, \theta, a_1, a_2]^T$ (see FIG. 16), the variables (i.e, $X_1$, $X_2$, $X_3$, and $X_4$) can be controlled to follow the specific path of the vasculature. It is assumed that G of the vasculature can be identified by using non-invasive imaging observations such as fluoroscopy or MRI and the curve has a constant curvature.

The intervention distance, s, in the form of a path variable, along the central line of the vessel is fed into the kinematic/static model with G and it generates references of n-th linear actuators, $X_{ref.n}$(n=1, 2, 3 and 4). Then $X_{ref}=[X_{ref.1}, X_{ref.2}, X_{ref.3}, X_{ref.4}]^T$, according to s in each vascular section (i.e., P1, P2, or P3 in FIG. 16) is follows:

$$X_{ref} = \begin{cases} [0, 0, 0, s]^T, \text{ if } s \in P1 \\ [f(\kappa, s - a_1), s - a_1, 0, s]^T, \text{ if } s \in P2 \\ [f(\kappa, \delta\theta), \delta\theta, s - a_1 - \delta\theta, a_1 + \delta\theta]^T, \text{ if } s \in P3 \end{cases} \tag{11}$$

Figure 17B:
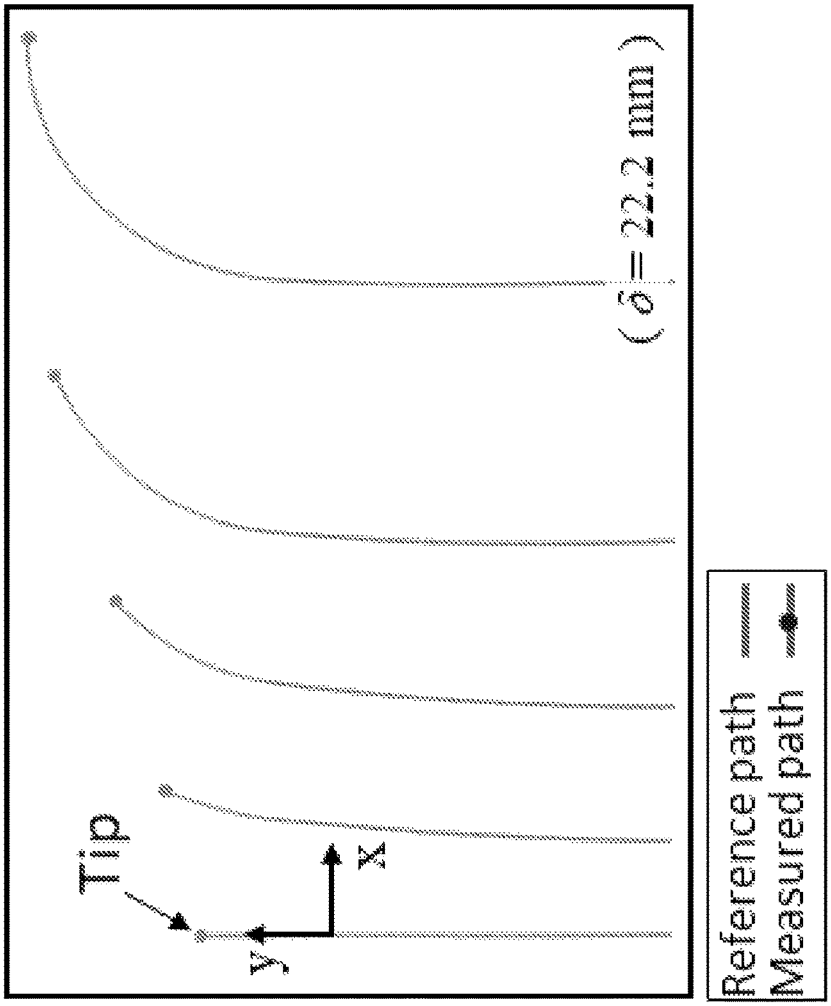
FIG. 17B illustrates the demonstration of the follow-the-leader motion with δ=22.2 mm.
Figure 17A:
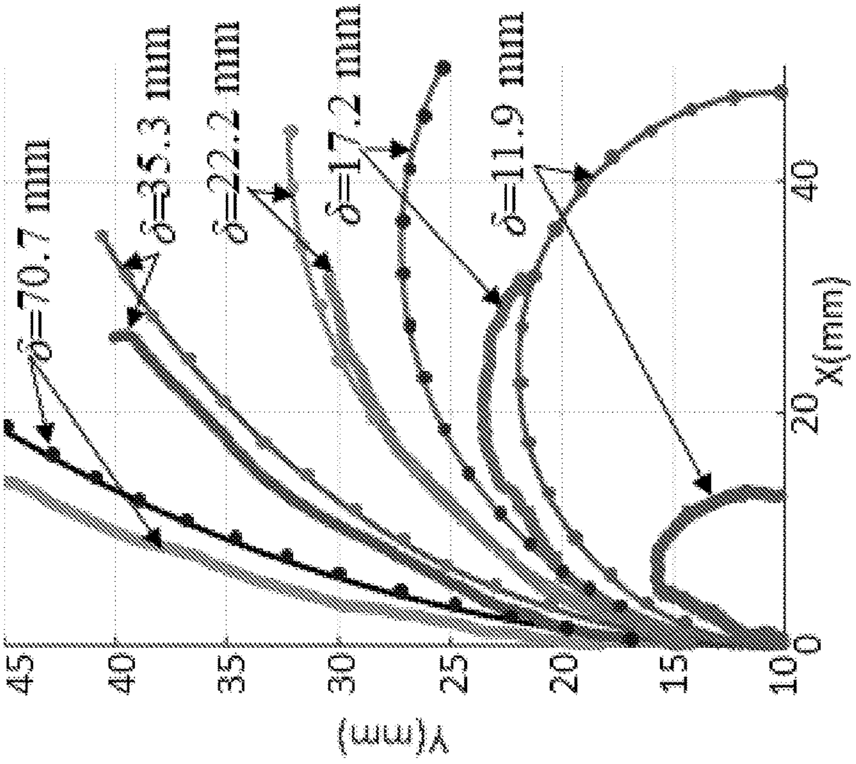
FIG. 17A illustrates follow-the-leader motions of the guidewire with respect to given reference paths in free space.
Figures 18A, 18B, 18C, 18D:
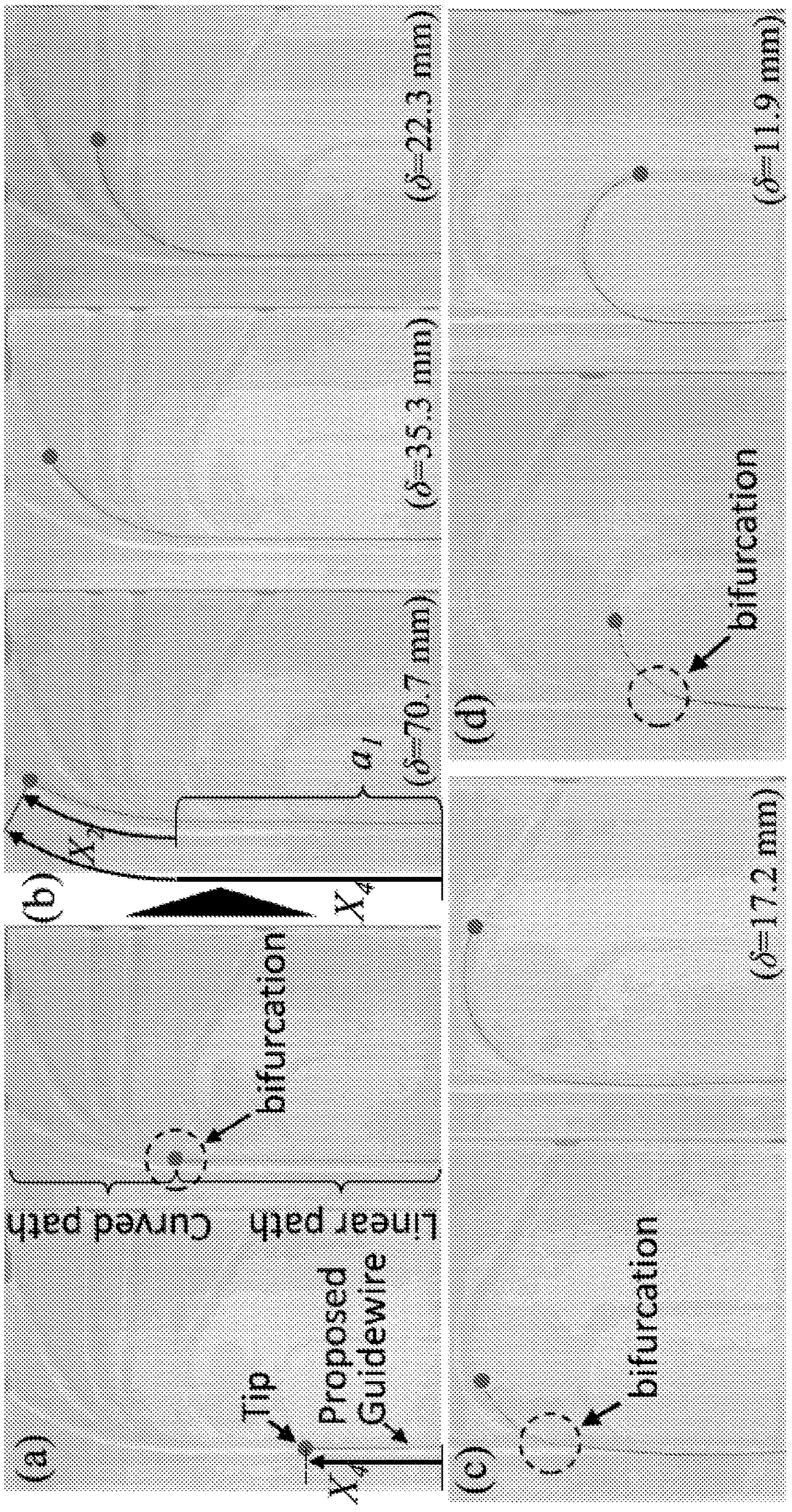
FIG. 18A shows the guidewire is advanced to a point of bifurcations in a linear path, FIGS. 18B-D. Given an $X_{ref}$, the guidewire can advance along any of the channels in the bifurcation. A dot indicates the guidewire tip.
Figures 19A, 19B, 19C, 19D:
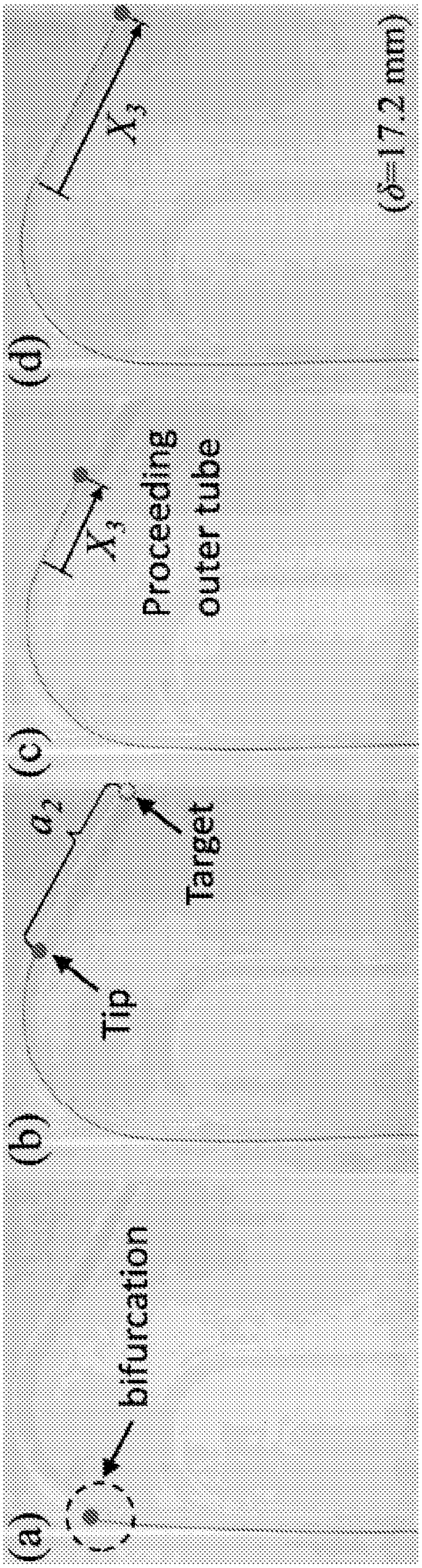
FIGS. 19A-19D shows the advancement of outer tube over the interior tubes after a vessel bifurcation has been successfully crossed (δ=17.2 mm).

FIGS. 17A, 17B show x-y coordinates of the tip following given reference curved paths with various curvatures by using the proposed control scheme in free space (here $a_1$ and $a_2$ are assumed to be 0) and were measured from the EM tracker in a single tracking trial. There are relatively small errors in low curvature paths (mean $L^2$ distance=4.53 mm); however, the error significantly increases in paths having high curvatures (mean $L^2$ distance=14.66 mm). It is believed this mainly occurs from the coupling of SB and SC, which shifts the coordinates of the SA. However, it is to be noted that this robot is meant to be actuated in a constrained space and this coupling issue can be compensated in the constrained space like vasculature.

To validate the present invention, a vascular phantom model replicating pediatric carotid arteries, aortic arches, and the aortic bifurcation with a range of curvatures between 0.08 $mm^{-1}$ and 0.015 $mm^{-1}$ was 3D-printed with various paths (see FIGS. 18A-18D). The guidewire was fed into a linear passage ($s \in P1$ in Equation (11)) and makes a curved shape of constant curvature to follow the given reference path at a bifurcation ($s \in P2$ in Equation (11)).

When the distal tip of the robot reaches the end of the curved path, the outer tube slides over the curved intermediate tube ($s \in P3$ in Equation (11)) and proceeds further (see FIGS. 19A-19D), which can provide the stable passage for the intermediate tube to reach the next operational point as the introducer sheath. The entire procedure is repeated at the next curved path.

The intervention and navigation function of the guidewire of the present invention was therefore successfully demonstrated at bifurcations with various curvatures in the vascular phantom model. This feature can prevent the kinking and breakage issues common with guidewires in current clinical practice without replacement of the guidewire and provide a stable and fast intervention process to treat CVDs in a minimally invasive manner.

The present innovation is a coaxially aligned steerable guidewire robot designed using coaxial tubes (in an exemplary embodiment, three) and a tendon (in an exemplary embodiment, one). Independent control of the bending arc length and the curvature allows the robot to follow the vascular curvatures of varying lengths and bending angles using its inherent follow-the-leader motion.

Kinematic and static models of the robot were derived, and a control algorithm proposed based on these models to control the present invention. This prototype of the robot has a diameter compatible with commercially used guidewires. The performance of the present invention was evaluated in free space and with a phantom vascular model. The robot successfully passes through several high curvature vascular structures. The present invention may also be capable of navigation through three-dimensional phantom vasculature with vascular stiffness properties and a pulsatile blood flow system under fluoroscopic guidance.

While certain embodiments of the disclosed technology have been described in connection with what is presently considered to be the most practical embodiments, it is to be understood that the disclosed technology is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the disclosed technology, including the best mode, and also to enable any person skilled in the art to practice certain embodiments of the disclosed technology, including making and using any devices or systems and performing any incorporated methods. The patentable scope of certain embodiments of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:

a path-providing guide comprising:

an arrangement of guide elements; and at least one tendon:

routed through an inner channel of an inner guide element of the arrangement of guide elements; and attached to an intermediate guide element of the arrangement of guide elements;

wherein the inner guide element is rotationally displaceable within the intermediate guide element; and a control unit operably connected to the path-providing guide;

wherein the path-providing guide and control unit are cooperatively configured to control:

a curvature of at least a portion of the path-providing guide; and an arc length of at least a portion of the path-providing guide via a relative position of the inner guide element among a telescopic displacement of an arrangement of one or more of other guide elements different from the inner guide element.

2. The system of claim 1, wherein:

the path-providing guide is configured to locate a distal end thereof to a destination; and the path-providing guide and control unit are cooperatively configured to independently control:

the curvature of the at least portion of the path-providing guide via activation of the tendon; and the arc length of the at least portion of the path-providing guide via the relative position of the inner guide element among the telescopic displacement of the arrangement of the one or more of other guide elements different from the inner guide element.

3. The system of claim 1, wherein:

the control unit is selected from the group consisting of a manually operable control unit and an automated control unit; and the system is selected from the group consisting of a manually steerable guidewire system with the manually operable control unit and a robotically steerable guidewire system with the automated control unit.

4. The system of claim 1, wherein:

the arrangement of guide elements is selected from a group consisting of a telescoping arrangement of nestable elements and a coaxial arrangement of tubular guide elements; and the control unit is configured to at least one of:

control a relative axial arrangement of the guide elements;

control a relative telescopic arrangement of the guide elements;

control a relative rotational arrangement of the guide elements; or control a stroke of the tendon.

5. The system of claim 1, wherein:

the path-providing guide has a variable stiffness profile along a length of the path-providing guide; and the path-providing guide and control unit are cooperatively configured to simultaneously and independently control both:

the curvature of the at least portion of the path-providing guide; and the arc length of the at least portion of the path-providing guide via the relative position of the inner guide element among the telescopic displacement of the arrangement of the one or more of other guide elements different from the inner guide element.

6. The system of claim 5, wherein the variable stiffness profile is continuously variable along the length of the path-providing guide.

7. The system of claim 5, wherein:

the variable stiffness profile is discretely variable along the length of the path-providing guide; and along one or more sections of the path-providing guide, the one or more sections have substantially a same stiffness along a length of the one or more sections.

8. The system of claim 1, wherein:

the path-providing guide has a proximal portion and a distal portion;

the tendon is attached to a distal end of the intermediate guide element;

the arrangement of guide elements comprises:

the inner guide element with the inner channel;

the intermediate guide element; and an outer guide element;

wherein one or more of the guide elements have a stiffness feature along at least a portion of a length of the respective guide element; and the guide elements each have suitable cross-sectional dimensions such that:

the inner guide element is further telescopically displaceable within the intermediate guide element;

the intermediate guide element is rotationally and telescopically displaceable within the outer guide element; and the outer guide element is rotationally and telescopically displaceable over the intermediate guide element.

9. The system of claim 8, wherein:

the intermediate guide element has a length defined from a proximal end to a distal end, and has a stiffness feature comprising a set of notches that begin at an intermediate location of the intermediate guide element and extend to the distal end of the intermediate guide element;

the outer guide element has a length defined from a proximal end to a distal end, and has a stiffness feature comprising a set of notches that begin at an intermediate location of the outer guide element and extend to the distal end of the outer guide element; and the set of notches of the outer guide element have a phase difference from the set of notches of the intermediate guide element enabling the intermediate guide element to be operationally rotational and telescopically displaceable within the outer guide element.

10. The system of claim 9, wherein:

the sets of notches form unidirectional asymmetric notch joints of the intermediate guide element and the outer guide element; and the phase difference of the sets of notches is 180°.

11. The system of claim 9, wherein:

the path-providing guide further has an intermediate portion;

a stiffness of the proximal portion of the path-providing guide is greater than a stiffness of the intermediate portion of the path-providing guide; and the stiffness of the intermediate portion of the path-providing guide is greater than a stiffness of the distal portion of the path-providing guide.

12. The system of claim 11, wherein a stiffness profile along a length of the path-providing guide is defined by a relative axial arrangement of the guide elements, a relative telescopic arrangement of the guide elements, a relative rotational arrangement of the guide elements, and a stroke of the tendon, such that:

the proximal portion of the path-providing guide is a length of the path-providing guide comprising the arrangement of a first portion of inner guide element, a first portion of the intermediate guide element that is without the set of notches, and a first portion of the outer guide element that is with the set of notches;

the intermediate portion of the path-providing guide is a length of the path-providing guide comprising the arrangement of a second portion of the inner guide element, a second portion of the intermediate guide element that is with the set of notches, and a second portion of the outer guide element that is with the set of notches, wherein the first portion and the second portion of the inner guide element comprise a full length of the inner guide element; and the distal portion of the path-providing guide is a length of the path-providing guide comprising the arrangement of a third portion of the intermediate guide element that is with the set of notches, and a third portion of the outer guide element that is with the set of notches.

13. The system of claim 9, wherein a length of the set of notches of the outer guide element is greater than a length of the set of notches of the intermediate guide element.

14. The system of claim 1, wherein:

the path-providing guide and control unit are cooperatively configured to simultaneously and independently control both:

the curvature of the at least portion of the path-providing guide via activation of the tendon; and the arc length of the at least portion of the path-providing guide via the relative position of the inner guide element among the telescopic displacement of the arrangement of the one or more of other guide elements different from the inner guide element; and a stiffness profile along a length of the path-providing guide is defined by a relative axial arrangement of the guide elements, a relative telescopic arrangement of the guide elements, a relative rotational arrangement of the guide elements, and a stroke of the tendon.

15. The system of claim 1, wherein:

the system is a robotically steerable guidewire system;

the arrangement of guide elements of the path-providing guide comprise at least three tubular elements:

the inner guide element being an inner tubular element with the inner channel;

the intermediate guide element being a first intermediate tubular element having a stiffness feature along at least a portion of a length of the intermediate tubular element; and an outer tubular element having a stiffness feature along at least a portion of a length of the outer tubular element;

the control unit is a control module;

the control module is configured to:

telescopically displace a relative position of the inner tubular element to the first intermediate tubular element;

rotationally displace a relative position of the first intermediate tubular element to the outer tubular element; and telescopically displace a relative position of the outer tubular element to the first intermediate tubular element;

one or more of the displacements of the tubular elements results in zones of stiffness along a length of the path-providing guide, a proximal zone having a greater stiffness than an intermediate zone, and the intermediate zone having a greater stiffness than a distal zone; and a guide element of the arrangement of guide elements is operationally configurable to be directed to a destination via a variable flexibility and arc length of the intermediate and distal zones of the path-providing guide.

16. The system of claim 1, wherein:

the path-providing guide is configured to provide a path for a delivery to a destination; and the path-providing guide and control unit are cooperatively configured to independently control:

the curvature of the at least portion of the path-providing guide via activation of the tendon; and the arc length of the at least portion of the path-providing guide via the relative position of the inner guide element among the telescopic displacement of the arrangement of the one or more of other guide elements different from the inner guide element.

17. A method of manipulating the system of claim 1 comprising:

locating a distal end of the path-providing guide to a destination; and simultaneously and independently controlling with the path-providing guide and control unit:

the curvature of the at least portion of the path-providing guide via activation of the tendon; and the arc length of the at least portion of the path-providing guide via the relative position of the inner guide element among the telescopic displacement of the arrangement of the one or more of other guide elements different from the inner guide element.

18. The method of claim 17, wherein:

simultaneously and independently controlling comprises at least one of:

controlling a relative axial arrangement of the guide elements;

controlling a relative telescopic arrangement of the guide elements;

controlling a relative rotational arrangement of the guide elements; or controlling a stroke of the tendon.

19. The method of claim 18, wherein:

the arrangement of guide elements comprises:

the inner guide element with the inner channel;

the intermediate guide element having a stiffness feature along at least a portion of a length of the intermediate guide element; and one or more additional guide elements, one of the additional guide elements being an outer guide element having a stiffness feature along at least a portion of a length of the outer guide element; and the guide elements each have suitable cross-sectional dimensions such that simultaneously and independently controlling further comprises:

rotationally and telescopically displacing the inner guide element within the intermediate guide element; and rotationally and telescopically displacing the intermediate guide element within the outer guide element.

20. A system comprising:

a path-providing guide comprising an arrangement of guide elements; and a control unit operably connected to the path-providing guide;

wherein the path-providing guide and control unit are cooperatively configured to simultaneously and independently control both:

a curvature of at least a portion of the path-providing guide; and an arc length of at least a portion of the path-providing guide via a relative position of an inner guide element of the guide elements among a telescopic displacement of an arrangement of one or more of other guide elements different from the inner guide element.

21. The system of claim 20, wherein:

the path-providing guide is configured to locate a distal end thereof to a destination;

the path-providing guide has a proximal portion and a distal portion; and the path-providing guide and control unit are cooperatively configured to simultaneously and independently control both:

the curvature of the distal portion of the path-providing guide; and the arc length of the distal portion of the path-providing guide via the relative position of the inner guide element among the telescopic displacement of the arrangement of the one or more of other guide elements different from the inner guide element.

22. The system of claim 20, wherein:

the arrangement of guide elements comprises at least the inner guide element and an intermediate guide element; and the path-providing guide further comprises a tendon routed through an inner channel of the inner guide element and attached to the intermediate guide element.

23. The system of claim 20, wherein:

the arrangement of guide elements is selected from a group consisting of a telescoping arrangement of nestable guide elements and a coaxial arrangement of tubular guide elements; and the control unit is configured to at least one of:

control a relative axial arrangement of the guide elements;

control a relative telescopic arrangement of the guide elements; or control a relative rotational arrangement of the guide elements.

24. A system comprising:

a path-providing guide comprising:

an arrangement of guide elements comprising at least a first guide element and a second guide element, the first guide element being rotationally displaceable within the second guide element; and at least one tendon:

routed through an inner channel of the first guide element; and attached to the second guide element; and a control unit operably connected to the path-providing guide;

wherein the path-providing guide and control unit are cooperatively configured to control:

a curvature of at least a portion of the path-providing guide via activation of the tendon; and an arc length of at least a portion of the path-providing guide via a relative position of the first guide element among a telescopic displacement of an arrangement of one or more of other guide elements different from the first guide element.

25. The system of claim 24, wherein:

the first guide element has a stiffness feature comprising a set of notches;

the second guide element has a stiffness feature comprising a set of notches; and the path-providing guide and control unit are cooperatively configured to independently and simultaneously control both:

the curvature of the at least portion of the path-providing guide; and the arc length of the at least portion of the path-providing guide via the relative position of the first guide element among the telescopic displacement of the arrangement of the one or more of other guide elements different from the first guide element.

26. A system comprising:

a path-providing guide comprising:

an arrangement of three or more sequential guide elements, the arrangement extending from a first of the sequential guide elements to a last of the sequential guide elements; and at least one tendon routed through an inner channel of the first of the sequential guide elements and attached to a second of the sequential guide elements; and a control unit operably connected to the path-providing guide;

wherein:

the second of the sequential guide elements has greater cross-sectional dimensions than the first of the sequential guide elements;

the first of the sequential guide elements is rotationally and telescopically displaceable within at least a portion of the second of the sequential guide elements;

each subsequent one of the sequential guide elements from a third of the sequential guide elements to the last of the sequential guide elements has greater cross-sectional dimensions than a respective previous one of the sequential guide elements;

each respective previous one of the sequential guide elements is rotationally and telescopically displaceable within at least a portion of the respective subsequent one of the sequential guide elements;

two or more of the sequential guide elements each have a stiffness feature comprising notches extending along at least a portion of a length of the respective sequential guide element;

an interplay between the notches varies a stiffness along a length of the path-providing guide; and the path-providing guide and control unit are cooperatively configured to control:

a curvature of at least a portion of the path-providing guide; and an arc length of at least a portion of the path-providing guide via a relative position of the first of the sequential guide elements among a telescopic displacement of an arrangement of one or more of other of the sequential guide elements different from the first of the sequential guide elements.

27. The system of claim 26, wherein the control of at least one of the curvature of the at least portion of the path-providing guide or the arc length of the at least portion of the path-providing guide further comprises control of at least one of:

control of a relative axial arrangement of the sequential guide elements;

control of a relative telescopic arrangement of the sequential guide elements;

control of a relative rotational arrangement of the sequential guide elements; or control of a stroke of at least one tendon.

28. The system of claim 26, wherein the path-providing guide and control unit are cooperatively configured to independently and simultaneously control both:

the curvature of the at least portion of the path-providing guide; and the arc length of the at least portion of the path-providing guide via the relative position of the first of the sequential guide elements among the telescopic displacement of the arrangement of the one or more of other of the sequential guide elements different from the first of the sequential guide elements.

29. The system of claim 26, wherein:

the system is a robotically steerable guidewire system;

one or more of the displacements of the sequential guide elements results in zones of stiffness along a length of the path-providing guide, a proximal zone having a greater stiffness than an intermediate zone, and the intermediate zone having a greater stiffness than a distal zone; and the last of the sequential guide elements is operationally configurable to be directed to a destination via a variable flexibility and arc length of the intermediate and distal zones of the path-providing guide.

* * * * *